United States Patent [19]
Christensen et al.

[11] Patent Number: 6,013,452
[45] Date of Patent: Jan. 11, 2000

[54] FUNGUS WHEREIN THE AREA, PEPC AND/ OR PEPE GENES HAVE BEEN INACTIVATED

[75] Inventors: Tove Christensen, Lyngby; Jan Lehmbeck, Vekso, both of Denmark

[73] Assignee: Novo Nordisk A/S, Bagsvaerd, Denmark

[21] Appl. No.: 09/079,415

[22] Filed: May 14, 1998

Related U.S. Application Data

[63] Continuation of application No. PCT/DK96/00528, Dec. 16, 1996.

[30] Foreign Application Priority Data

Dec. 15, 1995 [DK] Denmark ................................ 1428/95

[51] Int. Cl.[7] ...................................................... C12Q 1/68
[52] U.S. Cl. ............................ 435/6; 435/69.1; 435/225; 435/254.11; 435/254.21
[58] Field of Search .......................... 435/254.11, 254.21, 435/320.1, 225, 6, 69.1

[56] References Cited

U.S. PATENT DOCUMENTS

| | | | |
|---|---|---|---|
| 5,179,003 | 1/1993 | Wolf et al. | 435/69.1 |
| 5,190,931 | 3/1993 | Inouye et al. | 435/91.1 |
| 5,674,728 | 10/1997 | Buxton et al. | 435/225 |

FOREIGN PATENT DOCUMENTS

| | | |
|---|---|---|
| 0 184 438 | 6/1986 | European Pat. Off. . |
| 0 206 783 | 12/1986 | European Pat. Off. . |
| 0 238 023 | 9/1987 | European Pat. Off. . |
| 0 574 347 | 12/1993 | European Pat. Off. . |
| WO 90/00192 | 1/1990 | WIPO . |
| WO 92/17595 | 10/1992 | WIPO . |
| WO 95/35385 | 12/1995 | WIPO . |

OTHER PUBLICATIONS

EMBO Worshop, Ambleside, U.K. Sep. 2–7, 1995.
Christensen et al., (1998) Applied & Environmental Microbiology pp. 3232–3237.
Fu et al., (1990) 4(11):1847–1852.
Xiao Dong Xiao et al., (1993) 24:212–218.
Ying–Hui Fu et al., (1990) Molec. and Cellular Biol. 1056–1065.
B. L. Cohen (1981) Trans. Br. Mycol. Soc. 76(3):447–450.
B. L. Cohen (1972) J. of Gen. Microbiology 71:293–299.
B. L. Cohen (1973) J. of Gen. Microbiology 79:311–320.
Stankovich et al., (1993) Molecular Microbiology 7(1):81–87.
Books of Abstracts, 2nd Eur. Conf. on Jungal Genetics 4/28–5/194 1 page.
Upshall et al., (1987) Bio/Technology 5:1301–1304.
Caddick et al., (1986) The EMBO Journal 5(5):1087–1090.
Caddick et al., (1990) Gene 95:123–127.
Kudla et al., (1990) The EMBO Journal 9(5):1355–1364.
Arst, Jr. et al., Molec. gen. Genet., vol. 126, pp. 111–141 (1973).
Jarai et al., Gene, vol. 145, pp. 171–178 (1994).
Frederick et al., Gene, vol. 125, pp. 57–64 (1993).

*Primary Examiner*—James Ketter
*Attorney, Agent, or Firm*—Steve T. Zelson, Esq.; Reza Green, Esq.

[57] ABSTRACT

The present invention relates to fungi, which do not produce proteases. The fungi of the invention are useful as hosts for the production of proteins susceptible of proteolytic degradation by the proteases usually produced, and the invention consequently encompasses processes for the production of proteins of interest in high yields by using the fungi of the invention. The invention also comprises methods for producing such fungi and DNA constructs to be used in these methods.

35 Claims, 17 Drawing Sheets

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 2454 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Aspergillus oryzae (ix) FEATURE:
      (A) NAME/KEY: exon
      (B) LOCATION:603..701

(ix) FEATURE:
      (A) NAME/KEY: intron
      (B) LOCATION:702..791

(ix) FEATURE:
      (A) NAME/KEY: exon (B) LOCATION:792..942

(ix) FEATURE:
               (A) NAME/KEY: intron
               (B) LOCATION:943..1001

(ix) FEATURE:
               (A) NAME/KEY: exon
               (B) LOCATION:1002..1656

(ix) FEATURE:
               (A) NAME/KEY: intron
               (B) LOCATION:1657..1713

(ix) FEATURE:
               (A) NAME/KEY: exon
               (B) LOCATION:1714..2001

(ix) FEATURE:
               (A) NAME/KEY: CDS
               (B) LOCATION:join(603-701, 792-942, 1002-1656, 1714-2001)

(ix) FEATURE:
               (A) NAME/KEY: mat_peptide
               (B) LOCATION:603..2001

(xi) SEQUENCE DESCRIPTION: SEQ ID NO: 1:

```
GCGCGGATGT ACATTGTAGG TACATGGATA GTATGTACTG TATATACCGT CATTTAGTAA      60

GGCAACTAAC TAACTTATCA GCCTAGCTCC CGAGACGGCC TTACATCATC CGCAGCGGCA     120

ATCAGCTCCA CACCCTTGGA TAGTGATAAG AGACACAAGG AGTTCTGAGT ATGGTATTAT     180

AAGTGCAGTG AGTTGGGATG AAACAGAGAG ATAGAGGGAA TACTCCTATT TATCAATGAA     240

CGTATACAGA CATACCCCAG CAGCGTTCCT GGCGGTATTG TAAAAGGGCC GTACCTTGGA     300

GATCAAGTGA TGAGACACCC GTGATGCAGG AACTCCACTT CAATCCAATG ACGCATCGAG     360

TTGCTCCCTG ATTGGTTGAT ACGCAGGTCG CTCCGCAACC GGTCCGCATC ACCTCACTTC     420

CCTCCCCCAG ACCTGGAGGT ACCTCTCCCG TCCTTCTCTC CCTCTCCATC CCATCATCTA     480

TCCCTCTCCA GACCCTGATT GTATTTCATC ATTCCTATCG TCCCATATTA ATAGAGTATT     540

GCTAGTTTTC TTTTGATTTC GTCTGTTGAG GTGCTGCTTT TTTGTCGCCG TTGTCGCCCA     600
```

```
CC ATG AAG TCG ACC TTG GTT ACG GCC TCT GTG CTG TTG GGC TGT GCT          647
   Met Lys Ser Thr Leu Val Thr Ala Ser Val Leu Leu Gly Cys Ala
    1               5                  10                  15

TCC GCC GAG GTT CAC AAG CTG AAG CTC AAC AAG GTG CCC GTG TCC GAG          695
Ser Ala Glu Val His Lys Leu Lys Leu Asn Lys Val Pro Val Ser Glu
                 20                  25                  30

CAA TTT GTGAGTAGAC CTTACTATTC CGGCCATGAA AATATTCATC TACCCATCTG          751
Gln Phe

AAAGCTTGTC GGGACGAATT TCTGACTAAA TCGTATCCAG AAC TTG CAC AAC ATC         806
                                              Asn Leu His Asn Ile
                                                       35

GAC ACC CAT GTG CAG GCT CTC GGC CAG AAG TAC ATG GGA ATC CGT CCC          854
Asp Thr His Val Gln Ala Leu Gly Gln Lys Tyr Met Gly Ile Arg Pro
         40                  45                  50

AAC ATC AAG CAA GAT CTT CTC AAT GAG AAC CCG ATT AAC GAT ATG GGA          902
Asn Ile Lys Gln Asp Leu Leu Asn Glu Asn Pro Ile Asn Asp Met Gly
 55                  60                  65                  70

CGT CAT GAT GTC CTT GTT GAC AAC TTC CTG AAT GCA CAA T                    942
Arg His Asp Val Leu Val Asp Asn Phe Leu Asn Ala Gln
                 75                  80

GTACGAAACC CTAGTAATAC TTGAAGGGGG GCTCCAACTT ACGCGTAGAT TCTCTAAAG AC    1003
                                                                   Tyr

TTC TCC GAA ATC GAG ATC GGT ACT CCT CCA CAG AAG TTC AAG GTG GTC         1051
Phe Ser Glu Ile Glu Ile Gly Thr Pro Pro Gln Lys Phe Lys Val Val
```

```
                    85                      90                         95                        100
CTT GAC ACT GGC AGC TCA AAC CTA TGG GTG CCC TCT TCG GAG TGT GGT                                    1099
Leu Asp Thr Gly Ser Ser Asn Leu Trp Val Pro Ser Ser Glu Cys Gly
                    105                     110                 115

TCT ATC GCC TGC TAT TTG CAT AAC AAG TAC GAC TCA TCC TCG TCC TCC                                    1147
Ser Ile Ala Cys Tyr Leu His Asn Lys Tyr Asp Ser Ser Ser Ser Ser
                120                 125                 130

ACG TAC CAG AAG AAT GGC AGC GAA TTT GCC ATC AAG TAC GGC TCT GGT                                    1195
Thr Tyr Gln Lys Asn Gly Ser Glu Phe Ala Ile Lys Tyr Gly Ser Gly
            135                 140                 145

AGC CTG AGT GGT TTT GTT TCT CAG GAT ACT CTC AAG ATC GGT GAC CTG                                    1243
Ser Leu Ser Gly Phe Val Ser Gln Asp Thr Leu Lys Ile Gly Asp Leu
        150                 155                 160

AAG GTG AAG GAT CAG CTG TTC GCC GAG GCT ACT AGT GAG CCC GGC CTT                                    1291
Lys Val Lys Asp Gln Leu Phe Ala Glu Ala Thr Ser Glu Pro Gly Leu
165                 170                 175                 180

GCT TTT GCC TTT GGC CGC TTT GAT GGT ATC CTT GGG TTG GGA TTT GAC                                    1339
Ala Phe Ala Phe Gly Arg Phe Asp Gly Ile Leu Gly Leu Gly Phe Asp
                185                 190                 195

ACA ATT TCC GTC AAC AAG ATT CCT CCA CCC TTC TAT AGC ATG CTC GAC                                    1387
Thr Ile Ser Val Asn Lys Ile Pro Pro Pro Phe Tyr Ser Met Leu Asp
            200                 205                 210

CAG GGC CTC CTC GAC GAG CCA GTC TTT GCT TTC TAC CTT GGA GAC ACT                                    1435
Gln Gly Leu Leu Asp Glu Pro Val Phe Ala Phe Tyr Leu Gly Asp Thr
        215                 220                 225

AAC AAG GAA GGT GAT GAC TCC GTA GCG ACA TTC GGC GGT GTT GAC AAG                                    1483
Asn Lys Glu Gly Asp Asp Ser Val Ala Thr Phe Gly Gly Val Asp Lys
    230                 235                 240

GAT CAC TAC ACC GGC GAG TTG GTC AAG ATT CCC CTT CGC CGC AAG GCC                                    1531
Asp His Tyr Thr Gly Glu Leu Val Lys Ile Pro Leu Arg Arg Lys Ala
245                 250                 255                 260

TAC TGG GAG GTT GAC CTT GAT GCT ATC GCC CTT GGC GAT AGC GTT GCT                                    1579
Tyr Trp Glu Val Asp Leu Asp Ala Ile Ala Leu Gly Asp Ser Val Ala
                265                 270                 275

GAA CTC GAT AAC ACC GGT GTC ATT CTG GAT ACC GGC ACT TCC CTT ATC                                    1627
Glu Leu Asp Asn Thr Gly Val Ile Leu Asp Thr Gly Thr Ser Leu Ile
            280                 285                 290

GCC TTG GCC ACC ACC CTT GCC GAG CTT AT  GTAAGTCAAG CCAGTGTACT                                      1676
Ala Leu Ala Thr Thr Leu Ala Glu Leu Ile
        295                 300

GTGCATGTCT GTCATACTCT TACTAACTAT TCTGAAG T AAC AAG GAA ATC GGT                                     1729
                                          Asn Lys Glu Ile Gly
                                                      305

GCC AAG AAG GGC TTC ACC GGC CAA TAC TCG GTT GAC TGT GAC AAG CGC                                    1777
Ala Lys Lys Gly Phe Thr Gly Gln Tyr Ser Val Asp Cys Asp Lys Arg
        310                 315                 320

GAT TCC TTG CCT GAC CTC ACC TTC ACC CTG AGC GGA TAC AAC TTC ACC                                    1825
Asp Ser Leu Pro Asp Leu Thr Phe Thr Leu Ser Gly Tyr Asn Phe Thr
    325                 330                 335

ATT GGT CCC TAC GAC TAC ACT CTT GAA GTC CAG GGA TCT TGC ATC AGC                                    1873
Ile Gly Pro Tyr Asp Tyr Thr Leu Glu Val Gln Gly Ser Cys Ile Ser
340                 345                 350                 355

GCC TTC ATG GGC ATG GAC TTC CCT GAA CCC GTT GGC CCC TTG GCC ATC                                    1921
Ala Phe Met Gly Met Asp Phe Pro Glu Pro Val Gly Pro Leu Ala Ile
                360                 365                 370

CTG GGT GAC GCG TTC CTC AGG AAG TGG TAC AGT GTG TAC GAC CTC GCC                                    1969
Leu Gly Asp Ala Phe Leu Arg Lys Trp Tyr Ser Val Tyr Asp Leu Ala
            375                 380                 385

AAC GGT GCT GTT GGC CTG GCC AAG GCT AAG TAACCAAGTA ATCTACCATG                                      2019
Asn Gly Ala Val Gly Leu Ala Lys Ala Lys
```

```
                390               395
CTATGTTCTT ATTGGTTGCT TGTGTATGTG AGACAATGGT ACATGATAGC CTGCCTCGGT   2079

AGTTGGTTGG CCTTTTTCTG TTACGGGAAA TCGGCAAAGC CTTGTTTTCG CTTATGACCT   2139

CTATCCTGTT TGTTATTGAT ATTTTGTGTG ACTCAGTGAG CCACTGGCTA TGCTCTAATG   2199

ACATTCATTG GATGCCGATA GTTCTATATA CATTGCGATT TTAACGCGTA TCTTTGATCT   2259

ATCGGTACAA TGATTCCCTA CTAAAGGTAG CCCAACTAGA CAACTATGCC TACGACCTCT   2319

CTACATTCTT CATAGCTCCG TGTGGAGTCC GTCTCATACA ACCTCGAGCA ACCTGCAGTT   2379

CTTTGGTTAA CACAGACCAC ACCTTAAAAC GGCACGATCC ATTCGAATAG ACAAGCCCTC   2439

TTAATATTTG AATTC                                                   2454
```

(2) INFORMATION FOR SEQ ID NO: 2:

(i) SEQUENCE CHARACTERISTICS:
        (A) LENGTH: 397 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Ser Thr Leu Val Thr Ala Ser Val Leu Leu Gly Cys Ala Ser
 1               5                  10                  15

Ala Glu Val His Lys Leu Lys Leu Asn Lys Val Pro Val Ser Glu Gln
                20                  25                  30

Phe Asn Leu His Asn Ile Asp Thr His Val Gln Ala Leu Gly Gln Lys
            35                  40                  45

Tyr Met Gly Ile Arg Pro Asn Ile Lys Gln Asp Leu Leu Asn Glu Asn
    50                  55                  60

Pro Ile Asn Asp Met Gly Arg His Asp Val Leu Val Asp Asn Phe Leu
65                  70                  75                  80

Asn Ala Gln Tyr Phe Ser Glu Ile Glu Ile Gly Thr Pro Pro Gln Lys
                85                  90                  95

Phe Lys Val Val Leu Asp Thr Gly Ser Ser Asn Leu Trp Val Pro Ser
            100                 105                 110

Ser Glu Cys Gly Ser Ile Ala Cys Tyr Leu His Asn Lys Tyr Asp Ser
    115                 120                 125

Ser Ser Ser Ser Thr Tyr Gln Lys Asn Gly Ser Glu Phe Ala Ile Lys
130                 135                 140

Tyr Gly Ser Gly Ser Leu Ser Gly Phe Val Ser Gln Asp Thr Leu Lys
145                 150                 155                 160

Ile Gly Asp Leu Lys Val Lys Asp Gln Leu Phe Ala Glu Ala Thr Ser
                165                 170                 175

Glu Pro Gly Leu Ala Phe Ala Phe Gly Arg Phe Asp Gly Ile Leu Gly
            180                 185                 190

Leu Gly Phe Asp Thr Ile Ser Val Asn Lys Ile Pro Pro Pro Phe Tyr
    195                 200                 205

Ser Met Leu Asp Gln Gly Leu Leu Asp Glu Pro Val Phe Ala Phe Tyr
    210                 215                 220

Leu Gly Asp Thr Asn Lys Glu Gly Asp Asp Ser Val Ala Thr Phe Gly
225                 230                 235                 240

Gly Val Asp Lys Asp His Tyr Thr Gly Glu Leu Val Lys Ile Pro Leu
                245                 250                 255

Arg Arg Lys Ala Tyr Trp Glu Val Asp Leu Asp Ala Ile Ala Leu Gly
            260                 265                 270
```

```
Asp Ser Val Ala Glu Leu Asp Asn Thr Gly Val Ile Leu Asp Thr Gly
        275                 280                 285

Thr Ser Leu Ile Ala Leu Ala Thr Thr Leu Ala Glu Leu Ile Asn Lys
        290                 295                 300

Glu Ile Gly Ala Lys Lys Gly Phe Thr Gly Gln Tyr Ser Val Asp Cys
305                 310                 315                 320

Asp Lys Arg Asp Ser Leu Pro Asp Leu Thr Phe Thr Leu Ser Gly Tyr
                325                 330                 335

Asn Phe Thr Ile Gly Pro Tyr Asp Tyr Thr Leu Glu Val Gln Gly Ser
                340                 345                 350

Cys Ile Ser Ala Phe Met Gly Met Asp Phe Pro Glu Pro Val Gly Pro
        355                 360                 365

Leu Ala Ile Leu Gly Asp Ala Phe Leu Arg Lys Trp Tyr Ser Val Tyr
        370                 375                 380

Asp Leu Ala Asn Gly Ala Val Gly Leu Ala Lys Ala Lys
385                 390                 395
```

(2) INFORMATION FOR SEQ ID NO: 3:

(i) SEQUENCE CHARACTERISTICS:
        (A) LENGTH: 3224 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Aspergillus oryzae (ix) FEATURE:
        (A) NAME/KEY: exon
        (B) LOCATION:388..756

(ix) FEATURE:
        (A) NAME/KEY: intron
        (B) LOCATION:757..817

(ix) FEATURE:
        (A) NAME/KEY: exon
        (B) LOCATION:818..1753

(ix) FEATURE:
        (A) NAME/KEY: intron
        (B) LOCATION:1754..1814

(ix) FEATURE:
        (A) NAME/KEY: exon
        (B) LOCATION:1815..1997

(ix) FEATURE:
        (A) NAME/KEY: mat_peptide
        (B) LOCATION:388..1997

(ix) FEATURE:
        (A) NAME/KEY: CDS
        (B) LOCATION:join(388..756, 818..1753, 1815..1997)

(xi) SEQUENCE DESCRIPTION: SEQ ID NO: 3:

```
GGATCCATTA CCCTCTTACC GCCATACCCC AGGTCTTGCG ACCGCGCTAA TCGGGAGCGA        60

TCGACGCGCG GCACCTCCTC AGTAAAGCTG TGTCATCATT GTAAATTACC GTATCCCGGT       120

TGCATCATCC TCCGCTGCCC TTGCCTGCTT GGGGGATCGA CCTATTAAGC CCAGCTATCT       180

TACACCTGCT CCCATCCTCC TCTTCTCCAA CTCCTCATCC ATCCTTCCTC CTCCTTCTTC       240
```

```
CTTTTAACCC CCCCAACTCA GCATCGTTCC ATCCTCCCAT CTTTCCTTTC TTTTTACCTC        300

AAATCTCCAT CTGTATTCTT TCCTCTTAGA ACTCTTCCTT TCCCCCCTTC TGTACCTTGT        360

GTTTAGACGT CACTCTTGTT GCCCATC ATG AGA GGC ATC CTC GGC CTT TCC            411
                              Met Arg Gly Ile Leu Gly Leu Ser
                                1                   5

CTG CTG CCA CTA CTA GCA GCG GCC TCC CCC GTT GCT GTT GAC TCC ATC          459
Leu Leu Pro Leu Leu Ala Ala Ala Ser Pro Val Ala Val Asp Ser Ile
        10              15                  20

CAC AAC GGA GCG GCT CCC ATT CTT TCG GCC TCA AAT GCC AAA GAG GTT          507
His Asn Gly Ala Ala Pro Ile Leu Ser Ala Ser Asn Ala Lys Glu Val
    25              30                  35                  40

CCA GAC TCT TAC ATT GTC GTC TTC AAG AAG CAT GTT TCC GCT GAA ACG          555
Pro Asp Ser Tyr Ile Val Val Phe Lys Lys His Val Ser Ala Glu Thr
                45                  50                  55

GCT GCT GCT CAT CAC ACC TGG GTG CAG GAC ATC CAC GAT TCG ATG ACT          603
Ala Ala Ala His His Thr Trp Val Gln Asp Ile His Asp Ser Met Thr
            60                  65                  70

GGA CGC ATC GAC CTG AAG AAG CGC TCT CTT TTT GGT TTC AGT GAT GAC          651
Gly Arg Ile Asp Leu Lys Lys Arg Ser Leu Phe Gly Phe Ser Asp Asp
        75                  80                  85

CTT TAC CTC GGT CTC AAG AAC ACC TTC GAT ATC GCC GGG TCC CTA GCG          699
Leu Tyr Leu Gly Leu Lys Asn Thr Phe Asp Ile Ala Gly Ser Leu Ala
    90                  95                  100

GGC TAC TCC GGA CAT TTC CAT GAG GAT GTG ATC GAG CAG GTC CGG AGA          747
Gly Tyr Ser Gly His Phe His Glu Asp Val Ile Glu Gln Val Arg Arg
105             110                 115                 120

CAT CCT GAT GTAGGTTCCC CCCTCGGCCC ACCCGTTTTT GTAGAGCCCT                  796
His Pro Asp

TGGTCTAACT TGATTTTCAA G GTT GAA TAC ATC GAG AAA GAC ACC GAA GTC          847
                        Val Glu Tyr Ile Glu Lys Asp Thr Glu Val
                                125                 130

CAC ACC ATG GAG GAG ACA ACC GAG AAG AAT GCT CCC TGG GGC TTG GCT          895
His Thr Met Glu Glu Thr Thr Glu Lys Asn Ala Pro Trp Gly Leu Ala
        135                 140                 145

CGT ATC TCT CAC CGT GAC AGC CTC TCG TTC GGT ACC TTT AAC AAG TAC          943
Arg Ile Ser His Arg Asp Ser Leu Ser Phe Gly Thr Phe Asn Lys Tyr
150                 155                 160                 165

CTG TAT GCT TCG GAA GGC GGT GAG GGT GTC GAT GCT TAT ACT ATT GAC          991
Leu Tyr Ala Ser Glu Gly Gly Glu Gly Val Asp Ala Tyr Thr Ile Asp
                170                 175                 180

ACT GGT ATC AAC ATT GAG CAT GTC GAT TTC GAG GAT CGA GCA CAC TGG         1039
Thr Gly Ile Asn Ile Glu His Val Asp Phe Glu Asp Arg Ala His Trp
            185                 190                 195

GGA AAG ACC ATC CCT AGC AAT GAT GAG GAT GCG GAT GGC AAC GGA CAC         1087
Gly Lys Thr Ile Pro Ser Asn Asp Glu Asp Ala Asp Gly Asn Gly His
        200                 205                 210

GGA ACT CAC TGC TCC GGA ACC ATT GCT GGT AAG AAG TAC GGT GTT GCC         1135
Gly Thr His Cys Ser Gly Thr Ile Ala Gly Lys Lys Tyr Gly Val Ala
    215                 220                 225

AAG AAG GCC AAC ATC TAT GCC GTC AAG GTC TTG AGG TCC AGC GGT TCT         1183
Lys Lys Ala Asn Ile Tyr Ala Val Lys Val Leu Arg Ser Ser Gly Ser
230                 235                 240                 245

GGC ACT ATG TCC GAT GTC GTT CTG GGT GTC GAG TGG GCC GTC CAG TCC         1231
Gly Thr Met Ser Asp Val Val Leu Gly Val Glu Trp Ala Val Gln Ser
                250                 255                 260

CAC CTC AAG AAG GCT AAG GAC GCC AAA GAT GCC AAG GTC AAG GGT TTC         1279
His Leu Lys Lys Ala Lys Asp Ala Lys Asp Ala Lys Val Lys Gly Phe
            265                 270                 275
```

```
AAG GGC AGC GTT GCC AAC ATG AGT CTT GGT GGT GCC AAG TCC AGG ACC         1327
Lys Gly Ser Val Ala Asn Met Ser Leu Gly Gly Ala Lys Ser Arg Thr
        280                 285                 290

CTT GAG GCT GCT GTC AAT GCT GGT GTT GAG GCT GGT CTT CAC TTC GCC         1375
Leu Glu Ala Ala Val Asn Ala Gly Val Glu Ala Gly Leu His Phe Ala
    295                 300                 305

GTT GCT GCT GGT AAC GAC AAT GCC GAT GCC TGC AAC TAC TCC CCT GCT         1423
Val Ala Ala Gly Asn Asp Asn Ala Asp Ala Cys Asn Tyr Ser Pro Ala
310                 315                 320                 325

GCC GCT GAG AAT GCC ATC ACT GTC GGT GCC TCG ACC CTT CAG GAT GAG         1471
Ala Ala Glu Asn Ala Ile Thr Val Gly Ala Ser Thr Leu Gln Asp Glu
                330                 335                 340

CGT GCT TAC TTC TCC AAC TAC GGA AAG TGC ACT GAC ATC TTT GCC CCG         1519
Arg Ala Tyr Phe Ser Asn Tyr Gly Lys Cys Thr Asp Ile Phe Ala Pro
            345                 350                 355

GGT CCC AAC ATT CTT TCC ACC TGG ACT GGC AGC AAG CAC GCT GTC AAC         1567
Gly Pro Asn Ile Leu Ser Thr Trp Thr Gly Ser Lys His Ala Val Asn
        360                 365                 370

ACC ATC TCT GGA ACC TCT ATG GCT TCT CCT CAC ATT GCT GGT CTG CTG         1615
Thr Ile Ser Gly Thr Ser Met Ala Ser Pro His Ile Ala Gly Leu Leu
    375                 380                 385

GCC TAC TTC GTT TCT CTG CAG CCT GCT CAG GAC TCT GCT TTC GCT GTC         1663
Ala Tyr Phe Val Ser Leu Gln Pro Ala Gln Asp Ser Ala Phe Ala Val
390                 395                 400                 405

GAT GAG CTT ACT CCT GCC AAG CTC AAG AAG GAT ATC ATC TCC ATC GCC         1711
Asp Glu Leu Thr Pro Ala Lys Leu Lys Lys Asp Ile Ile Ser Ile Ala
                410                 415                 420

ACC CAG GGT GCC CTT ACT GAT ATC CCA TCT GAC ACC CCC AAC                 1753
Thr Gln Gly Ala Leu Thr Asp Ile Pro Ser Asp Thr Pro Asn
            425                 430                 435

GTAAGTTATA TTATCCATTT TGGTATAATG AAACAGAAAG TGGCTAACTG TTTTATTCTA       1813

G CTT CTC GCC TGG AAC GGC GGT GGT GCC GAC AAC TAC ACC CAG ATT          1859
  Leu Leu Ala Trp Asn Gly Gly Gly Ala Asp Asn Tyr Thr Gln Ile
                  440                 445                 450

GTC GCC AAG GGT GGA TAC AAG GCC GGT AGT GAC AAC CTT AAG GAC CGC         1907
Val Ala Lys Gly Gly Tyr Lys Ala Gly Ser Asp Asn Leu Lys Asp Arg
            455                 460                 465

TTT GAC GGA CTA GTC AAC AAG GCC GAG AAG TTG CTC GCT GAG GAG CTT         1955
Phe Asp Gly Leu Val Asn Lys Ala Glu Lys Leu Leu Ala Glu Glu Leu
        470                 475                 480

GGA GCT ATT TAC AGT GAG ATC CAG GGT GCT GTT GTT GCA TAG                 1997
Gly Ala Ile Tyr Ser Glu Ile Gln Gly Ala Val Val Ala  *
    485                 490                 495

ATGCAAGACA AGACTTGATT TAGAGTGACG TAACTAGTTT CGTTTATGGC AGGGTATGGG       2057

AATTGGCTAA CCGAACACTG GCGCTGGTAT TTGTTTTTGC TGCTGCTTTT TGGTAACACG       2117

GAGAAGCCGA TGCATTGACT GCATTGGGTA CATTATCCTG ACATGGTTTA CCTGGTCTTT       2177

CATTATTATT ATAGCATACA TGTCCACAAC AATCTTTGAC ATCCTATCTA GAGATACATG       2237

TGCTTGCTTT TAACAGACTG CCAAATCAAT TATGCGACTG TTCTGCACAG ATAATCGTGG       2297

CTTGGTTTGA AGGCTGCCAT AAAGTCTAAC GCTGGCTACC AATTAGGTAG GAGTGTCCCC       2357

TTCCTGCCAG GTTGCTCCAG TCGTAGAAGT AGACTGATAT ATTGAAGATT GCCCATATAC       2417

CATGGACGCT CGTCTTATTC TACATCATAT ATGTCACTCC TAGTGACCAT ATAGACATGC       2477

TAACCATTGC ACAACCCCCC ACAGGTTCAA TCCAACCCAT GACCCCTCT CATCTTCTGT        2537

TGTATTTTCA GGTTCTAGAT TTGCATACAT ACTACCCATC ATCGGAAGAC GGGTGAGGAG       2597

GCAGATGACC CGACATTATA TTTATTAATT GCTTAGGATG TTTCAACAAC ATTAAAGTA       2657
```

```
TATCAATAAG CTTTTCCAGT TTATATTTAC TACCTAAGAT TACGGCATAT AGTGTATTCT    2717

GTGTGCGTAA GAGGTCGCCC TTAAATGGAA ACAGTTCGCG GTTGGAGATA TATATTTGTA    2777

GTGTTCAGGC GGAACGAGTA AAAAAAAAAA AAAATGAGAA GCTGGTGATA TTAACTCCGA    2837

TGTTTATCTT ACATATACCA ATGGATGTAG TCTCATTATA ACGCTTTCTC TGTAGTTTGG    2897

TTGTCATAGA ACTGAATGAC AGGTAAGTGT GTATGTATGT ACAGTACGCA CGGGGGGCCA    2957

TGTGGTCAAC CACACCCAAT GGGCGGTCTT GTCACTTTCC GGACTGGAAA TGAAACGTTC    3017

CATGGAAGAA ATCTGGATGA TTACCTTGAG TACGAGAGAA CTATGGTTGC CGGTAATGGG    3077

TGATTGCCAC AATCATCAGT TCGGTTGAGG CGTTCAACAT CTACGGTACG TTCAGTCACA    3137

TGAATCTGGG AATTCGGGCC TGGTATGCTG GTTTTCGCAA GAGATCCACC CGGCGTGTGC    3197

CAGGTATGCT ACATTTTCTC AGTCGAC                                        3224
```

(2) INFORMATION FOR SEQ ID NO: 4:

(i) SEQUENCE CHARACTERISTICS:
        (A) LENGTH: 495 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Arg Gly Ile Leu Gly Leu Ser Leu Leu Pro Leu Leu Ala Ala
 1               5                  10                  15

Ser Pro Val Ala Val Asp Ser Ile His Asn Gly Ala Ala Pro Ile Leu
            20                  25                  30

Ser Ala Ser Asn Ala Lys Glu Val Pro Asp Ser Tyr Ile Val Val Phe
        35                  40                  45

Lys Lys His Val Ser Ala Glu Thr Ala Ala Ala His His Thr Trp Val
    50                  55                  60

Gln Asp Ile His Asp Ser Met Thr Gly Arg Ile Asp Leu Lys Lys Arg
65                  70                  75                  80

Ser Leu Phe Gly Phe Ser Asp Asp Leu Tyr Leu Gly Leu Lys Asn Thr
                85                  90                  95

Phe Asp Ile Ala Gly Ser Leu Ala Gly Tyr Ser Gly His Phe His Glu
            100                 105                 110

Asp Val Ile Glu Gln Val Arg Arg His Pro Asp Val Glu Tyr Ile Glu
        115                 120                 125

Lys Asp Thr Glu Val His Thr Met Glu Glu Thr Glu Lys Asn Ala
    130                 135                 140

Pro Trp Gly Leu Ala Arg Ile Ser His Arg Asp Ser Leu Ser Phe Gly
145                 150                 155                 160

Thr Phe Asn Lys Tyr Leu Tyr Ala Ser Glu Gly Gly Glu Gly Val Asp
                165                 170                 175

Ala Tyr Thr Ile Asp Thr Gly Ile Asn Ile Glu His Val Asp Phe Glu
            180                 185                 190

Asp Arg Ala His Trp Gly Lys Thr Ile Pro Ser Asn Asp Glu Asp Ala
        195                 200                 205

Asp Gly Asn Gly His Gly Thr His Cys Ser Gly Thr Ile Ala Gly Lys
    210                 215                 220

Lys Tyr Gly Val Ala Lys Lys Ala Asn Ile Tyr Ala Val Lys Val Leu
225                 230                 235                 240

Arg Ser Ser Gly Ser Gly Thr Met Ser Asp Val Val Leu Gly Val Glu
                245                 250                 255
```

```
Trp Ala Val Gln Ser His Leu Lys Lys Ala Lys Asp Ala Lys Asp Ala
            260                 265                 270

Lys Val Lys Gly Phe Lys Gly Ser Val Ala Asn Met Ser Leu Gly Gly
        275                 280                 285

Ala Lys Ser Arg Thr Leu Glu Ala Ala Val Asn Ala Gly Val Glu Ala
    290                 295                 300

Gly Leu His Phe Ala Val Ala Gly Asn Asp Asn Ala Asp Ala Cys
305                 310                 315                 320

Asn Tyr Ser Pro Ala Ala Glu Asn Ala Ile Thr Val Gly Ala Ser
                325                 330                 335

Thr Leu Gln Asp Glu Arg Ala Tyr Phe Ser Asn Tyr Gly Lys Cys Thr
            340                 345                 350

Asp Ile Phe Ala Pro Gly Pro Asn Ile Leu Ser Thr Trp Thr Gly Ser
        355                 360                 365

Lys His Ala Val Asn Thr Ile Ser Gly Thr Ser Met Ala Ser Pro His
    370                 375                 380

Ile Ala Gly Leu Leu Ala Tyr Phe Val Ser Leu Gln Pro Ala Gln Asp
385                 390                 395                 400

Ser Ala Phe Ala Val Asp Glu Leu Thr Pro Ala Lys Leu Lys Lys Asp
                405                 410                 415

Ile Ile Ser Ile Ala Thr Gln Gly Ala Leu Thr Asp Ile Pro Ser Asp
            420                 425                 430

Thr Pro Asn Leu Leu Ala Trp Asn Gly Gly Gly Ala Asp Asn Tyr Thr
        435                 440                 445

Gln Ile Val Ala Lys Gly Gly Tyr Lys Ala Gly Ser Asp Asn Leu Lys
    450                 455                 460

Asp Arg Phe Asp Gly Leu Val Asn Lys Ala Glu Lys Leu Leu Ala Glu
465                 470                 475                 480

Glu Leu Gly Ala Ile Tyr Ser Glu Ile Gln Gly Ala Val Val Ala
                485                 490                 495

(2) INFORMATION FOR SEQ ID NO: 5:

(i) SEQUENCE CHARACTERISTICS:
        (A) LENGTH: 5643 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Aspergillus oryzae
        (B) STRAIN: IFO4177

(ix) FEATURE:
        (A) NAME/KEY: intron
        (B) LOCATION: 2701..2769

(ix) FEATURE:
        (A) NAME/KEY: CDS
        (B) LOCATION: join(2282..2700, 2770..4949)

(xi) SEQUENCE DESCRIPTION: SEQ ID NO: 5:

AAGCTTCGTC CTCGCATCTC GGCCGGGTGA GTAAGGTATG GTATTATTCA TGAAGGGATC      60

TCGTTGGTTA CCGTTGTCTA TCCCTAAACA AAGGATTCAA GAGAACAACT CGGAATGCTC     120

CCTCCGCTTA AACCCCTTGA CTCACTGATG GTGTATGTAC TATGGGTACG ACGTTCGGGA     180
```

-continued

| | |
|---|---|
| TGTGGACTAC CAACCAGAGA GTGATTAGAG AGTCCGGGTT CTCAGTCCAT GATTTTTGCA | 240 |
| TCTTTGAAAC AGACGATGCG GAGCGGTCAT TGGCGGAGTT TACTCCCAAA TACGGCCGAA | 300 |
| CGGGGTACTT TAAGTGGAAT CTCCGATTTT GGATCTAAGC TCATGAAGGA AAAGTACTAC | 360 |
| TAATGCGTAC CTGTGCCTAA TGTTAGTGCT AGTTCGTCTG TTGCATTTTA CCCGTCGGTT | 420 |
| AAGACGAATG GATCCGTTCA GGTTTTAAAA TAACTATCTA TGAAATATTT TAGATTTCCC | 480 |
| GACATAGTGG TTGGGATGTC TCGATTAACA CTAGGTACAT CAGGCTCAAT TGATTTTGGT | 540 |
| TTTAACGAAA CATGATATAG GTCAGGGTCG TGGACCACCC TCCGCCAGGG ATCAGGGGAC | 600 |
| GGTTACATGC GAAGGATTCT GATTATATTC ATGATTATGT CAAGCCTTTT CTCTCGTGTG | 660 |
| AAGAGGAGCA GAGAATCCGT ACGGGTTTAA TTTAATTTAG CGCCCTGCAG CTTCGAGAAC | 720 |
| ATCCCCAGCA ACGTTAAAAA CCACGAGCTA AAATGGGTCG CCACCGGAAG CACTCGAGTC | 780 |
| GAGAGATCGG TCGGCTCAGT ATTCGTAATA CCTGCGTTCC AGACGGTTTT GGTCGTTGGT | 840 |
| TTCACTCAGG GAACTTAATT CCAGCGGGAC CCAATATAAT TTGAATGATT CATGATACAT | 900 |
| CCATTCGTTT GAACCGATCC TGCAAGAGTT CTGTCTGATT TGGTCAACAT AGTTTTCCTC | 960 |
| TGGGGGAGAC TGGGGAAGAG TCAACACAAT GGTCAGGGAG AGAAGAATGA AAGCTCTCGC | 1020 |
| AAGTGGATGA TCATGCTACG TACTGTAGGA ATAAAATTAA TTAATGCGAG CTGCAAGTA | 1080 |
| TCCCTGCGCC GATTTCTCT TCTTACGGCG GGAACCAAAA AATGTGACGC TGTGATTTTC | 1140 |
| TGGAAAAGGT AAGGATGTTT AGTTTCCCAG GATTATTACT GGTTCCGTAT GTGTATGTGT | 1200 |
| ATGGATATCA TTCCGTATGG ATACGCCCGT TTCCTCCGCC CAGAACCAGT CCGTCATCCA | 1260 |
| TCCTCCACTC TTTCTTCTCT TAGAGCCTTT CCACCTCTCT TCACTTTCTT TTTCTTTCCC | 1320 |
| CCCTCCCTCT TTGCTTTCCC TCTCCCAGTA TTATTCTTAT ATTATCGGTT TGACCGTCGC | 1380 |
| CTCAGTATCG GCCCCCGTG AATCACTTTT CGTTTCTCTT GTATTTTACT TTCCTATCTG | 1440 |
| GGATTGCTCC TCGATTAGCA GCTCTACTTC ATTCGGCCAT GTGCGTCTAG AGGGTCTAGC | 1500 |
| CCCTCTCTCT CTTTGCACTG ACTGTCAGCC ATACCATAGT ATCATCCCGG AATTAAGAAA | 1560 |
| AAAAAAGAAA TTATTCTACC TCCGATCTGG ACAAATTATA ACCAGGAGAA AATCAAGCGA | 1620 |
| AAGAGGGGCA AAGGAGGAGA CACCATTAAA ACTGGGTCTG GTTTGATTCA TGACATACAT | 1680 |
| TCGTCGTCTT GAATTTCAAT AGGTACGGAC TGATGCATTC CACTCGAGCC TTTTTAGCTG | 1740 |
| CGTGTCCGTC TCCAATCGCA CTTCTTTTCT TATTTCCTTG TGGGATAAAT TGATTATTTA | 1800 |
| CCGTTTCGTT TTCTCTATAT TGCGGTGGTG GTGCGACCCA TCCAACTATT ATTATTATAA | 1860 |
| TTGGAATTTG ATTTGGATTT TGATTCCTGT GACGGATCTC AGACCAAGTG CCTAAACTAT | 1920 |
| AACTGACTTG GACCCCCTTC AGATCCTAGC TTCCCGATTC TTTTCCACCA CTGCTGCATC | 1980 |
| CTCTTCCTGC ACGCAGCGTT CGTTTAGGGC GGGTAGACTG GAATTTATTC CTTGCGCCAC | 2040 |
| GGACCAATCG CTCCCTCGAC GCTCTCATTC CTGCGTCGAG CTCTTTTTCC CTCGACTCTC | 2100 |
| ATTGCTTGCT GGGCTGGTTC TTGAACCTCT TCAATCGTCC TTATCTCTTT CCCCCCATCC | 2160 |
| GGCCTGTGAT TCCTATCTTT CCTTTTTTTC TTCCCTTTCT TGTTTGATCC CCCTCCTCC | 2220 |
| CCGTCTTATC GCCTACTATC GTGATCCCCG CCCTTCCCAA TAAAGAGTAG GGCGTGTGAA | 2280 |

| | |
|---|---|
| C ATG TCC GGG TTA ACC CTC GGG CGA GGC CCT GGG GGC GTG CGA CCG<br>  Met Ser Gly Leu Thr Leu Gly Arg Gly Pro Gly Gly Val Arg Pro<br>  1         5               10            15 | 2326 |
| ACT CAA ACC GCA ACT TTT ACC ACC CAC CAC CCG TCC GCC GAT GCT GAC<br>Thr Gln Thr Ala Thr Phe Thr Thr His His Pro Ser Ala Asp Ala Asp<br>            20             25            30 | 2374 |
| CGC TCC TCC AAC AAC CTC CCC CCT ACC TCC TCG CAG CTG TCC GAT GAC<br>Arg Ser Ser Asn Asn Leu Pro Pro Thr Ser Ser Gln Leu Ser Asp Asp | 2422 |

```
                    35                    40                     45
TTT TCT TTC GGT TCC CCT CTG AGC CCC GCC GAC TCA CAG GCC CAT GAC      2470
Phe Ser Phe Gly Ser Pro Leu Ser Pro Ala Asp Ser Gln Ala His Asp
            50                  55                  60

GGC CTA CTT CAG GAC TCC CTC TTC CCT GAA TGG GGG TCT GGT GCG CCT      2518
Gly Leu Leu Gln Asp Ser Leu Phe Pro Glu Trp Gly Ser Gly Ala Pro
        65                  70                  75

CGA CCC GGC ATT GAC AGT CCG GAT GAG ATG CAG AGG CAA GAT CCG CTA      2566
Arg Pro Gly Ile Asp Ser Pro Asp Glu Met Gln Arg Gln Asp Pro Leu
80                  85                  90                  95

GCG ACT CAA ATA TGG AAG CTC TAT TCT AGG ACC AAG GCC CAG TTG CCC      2614
Ala Thr Gln Ile Trp Lys Leu Tyr Ser Arg Thr Lys Ala Gln Leu Pro
                100                 105                 110

AAC CAG GAG CGT ATG GAA AAC CTG ACC TGG CGG ATG ATG GCG ATG AGT      2662
Asn Gln Glu Arg Met Glu Asn Leu Thr Trp Arg Met Met Ala Met Ser
            115                 120                 125

TTG AAA CGT AAG GAG CGG GAA CGT GCT CAA CAG TCC    AT GTAGGTGTTC     2710
Leu Lys Arg Lys Glu Arg Glu Arg Ala Gln Gln Ser    Met
        130                 135                    140

TCCCTCTGTA GAGGAACGGC TGGACCCGCT CATCATTAAT TTTTTTTTTG TCTGTGAAG G   2770

TTT CCT GCG AGA CGC GGT AGC GCT GGC CCC AGT GGT ATC GCT CAA CTG      2818
Phe Pro Ala Arg Arg Gly Ser Ala Gly Pro Ser Gly Ile Ala Gln Leu
                145                 150                 155

CGC ATT TCC GAC CCG CCC GTT GCC ACC GGT AAC CCT CAG TCA ACC GAC      2866
Arg Ile Ser Asp Pro Pro Val Ala Thr Gly Asn Pro Gln Ser Thr Asp
            160                 165                 170

CTG ACC GCC GAC CCT ATG AAC CTC GAC GAT TTC ATC GTG CCC TTC GAA      2914
Leu Thr Ala Asp Pro Met Asn Leu Asp Asp Phe Ile Val Pro Phe Glu
        175                 180                 185

TCT CCT TCG GAC CAC CCC TCG CCC AGT GCC GTC AAG ATT TCC GAC TCC      2962
Ser Pro Ser Asp His Pro Ser Pro Ser Ala Val Lys Ile Ser Asp Ser
    190                 195                 200

ACG GCG TCC GCG GCC ATT CCC ATC AAG TCC CGG AAA GAC CAG CTG AGA      3010
Thr Ala Ser Ala Ala Ile Pro Ile Lys Ser Arg Lys Asp Gln Leu Arg
205                 210                 215                 220

GAT TCT ACC CCG GTG CCG GCC TCG TTC CAC CAT CCG GCT CAG GAT CAA      3058
Asp Ser Thr Pro Val Pro Ala Ser Phe His His Pro Ala Gln Asp Gln
                225                 230                 235

CGG AAG AAC AGT GAA TTT GGC TAC GTC CCC CGT CGC GTG CGC AAG ACG      3106
Arg Lys Asn Ser Glu Phe Gly Tyr Val Pro Arg Arg Val Arg Lys Thr
            240                 245                 250

AGT ATC GAC GAG CGT CAA TTT TTC TCA CTG CAG GTG CCG ACC CGA AAG      3154
Ser Ile Asp Glu Arg Gln Phe Phe Ser Leu Gln Val Pro Thr Arg Lys
        255                 260                 265

CGA CCG GCC GAA TCC TCG CCC CAG GTA CCC CCC GTT TCC AAC TCG ATG      3202
Arg Pro Ala Glu Ser Ser Pro Gln Val Pro Pro Val Ser Asn Ser Met
    270                 275                 280

TTG GCC CAC GAT CCG GAC CTC GCT TCC GGC GTG CCC GAT TAT GCC TTG      3250
Leu Ala His Asp Pro Asp Leu Ala Ser Gly Val Pro Asp Tyr Ala Leu
285                 290                 295                 300

GAC GCC CCG TCG TCG GCC TTT GGC TTC CAT CAG GGT AAC CAC CAT CCG      3298
Asp Ala Pro Ser Ser Ala Phe Gly Phe His Gln Gly Asn His His Pro
                305                 310                 315

GTC AAT CAT CAC AAC CAC ACC TCC CCC GGG GCA CCG TTT GGC TTG GAT      3346
Val Asn His His Asn His Thr Ser Pro Gly Ala Pro Phe Gly Leu Asp
            320                 325                 330

ACG TTC GGC CTG GGA GAT GAT CCA ATC TTG CCC TCC GCG GGC CCC TAC      3394
Thr Phe Gly Leu Gly Asp Asp Pro Ile Leu Pro Ser Ala Gly Pro Tyr
        335                 340                 345
```

-continued

| | |
|---|---|
| CAG TCG CAA TTC ACC TTC TCA CCC AGC GAG TCT CCG ATG GCC TCC GGT<br>Gln Ser Gln Phe Thr Phe Ser Pro Ser Glu Ser Pro Met Ala Ser Gly<br>350     355     360 | 3442 |
| CAT CCG TTT GCG AAC CTC TAT TCG CAT ACC CCG GTG GCT TCG TCC CTC<br>His Pro Phe Ala Asn Leu Tyr Ser His Thr Pro Val Ala Ser Ser Leu<br>365     370     375     380 | 3490 |
| AAC TCG ACG GAT TTC TTC TCT CCA CCG CCA TCA GGC TAC CAG TCC ACG<br>Asn Ser Thr Asp Phe Phe Ser Pro Pro Pro Ser Gly Tyr Gln Ser Thr<br>     385     390     395 | 3538 |
| GCA TCC ACG CCG CAG CCC ACC TAC GAC GGG GAC CAT TCC GTT TAT TTC<br>Ala Ser Thr Pro Gln Pro Thr Tyr Asp Gly Asp His Ser Val Tyr Phe<br>400     405     410 | 3586 |
| GAT ATG CCG TCG GGC GAC GCG CGC ACC CAG CGC CGC ATT CCG AAC TAT<br>Asp Met Pro Ser Gly Asp Ala Arg Thr Gln Arg Arg Ile Pro Asn Tyr<br>415     420     425 | 3634 |
| ATT TCG CAT CGG TCC AAC TTG TCT GCT TCG CTG CAG CCT CGG TAT ATG<br>Ile Ser His Arg Ser Asn Leu Ser Ala Ser Leu Gln Pro Arg Tyr Met<br>430     435     440 | 3682 |
| TTC AAC CAG AAC AAC CAT GAA CAG GCC AGT TCG TCG ACG GTG CAT TCG<br>Phe Asn Gln Asn Asn His Glu Gln Ala Ser Ser Ser Thr Val His Ser<br>445     450     455     460 | 3730 |
| CCG AGC TAC CCC ATT CCC CAG CCG CAA CAT GTG GAC CCC ACT CAG GTG<br>Pro Ser Tyr Pro Ile Pro Gln Pro Gln His Val Asp Pro Thr Gln Val<br>     465     470     475 | 3778 |
| TTG AAC GCC ACC AAT TAC TCG ACC GGC AAC TCC CAC CAT ACC GGC GCC<br>Leu Asn Ala Thr Asn Tyr Ser Thr Gly Asn Ser His His Thr Gly Ala<br>480     485     490 | 3826 |
| ATG TTT TCA TTT GGA GCC GAT TCA GAT AAC GAG GAT GAC GAT GGT CAT<br>Met Phe Ser Phe Gly Ala Asp Ser Asp Asn Glu Asp Asp Asp Gly His<br>   495     500     505 | 3874 |
| CAG CTG TCC GAG CGG GCT GGT CTG GCG ATG CCG ACT GAA TAT GGG GAC<br>Gln Leu Ser Glu Arg Ala Gly Leu Ala Met Pro Thr Glu Tyr Gly Asp<br>510     515     520 | 3922 |
| GAG GAC GGG TTC TCG TCG GGC ATG CAG TGG GAT GGG CAG TTC CCG GGC<br>Glu Asp Gly Phe Ser Ser Gly Met Gln Trp Asp Gly Gln Phe Pro Gly<br>525     530     535     540 | 3970 |
| TCC TTC CAT TCG CTG CCG GGC TTT GGC CCT CAA CAT CGC AAG CAT GTT<br>Ser Phe His Ser Leu Pro Gly Phe Gly Pro Gln His Arg Lys His Val<br>     545     550     555 | 4018 |
| ACC ATC GGG TCC ACG GAC ATG ATG GAC ACC CCC GAG GAG TGG AAT CAC<br>Thr Ile Gly Ser Thr Asp Met Met Asp Thr Pro Glu Glu Trp Asn His<br>Thr Ile Gly Ser Thr Asp Met Met Asp Thr Pro Glu Glu Trp Asn His<br>   560     565     570 | 4066 |
| GGT GGC AGT TTG GGT CGG ACT CAT GGG TCG GTG GCT TCG GTC AGT GAG<br>Gly Gly Ser Leu Gly Arg Thr His Gly Ser Val Ala Ser Val Ser Glu<br>575     580     585 | 4114 |
| GTG CGC AAC CGA GAG CAG GAC CCT CGC CGG CAG AAG ATT GCC CGC ACC<br>Val Arg Asn Arg Glu Gln Asp Pro Arg Arg Gln Lys Ile Ala Arg Thr<br>590     595     600 | 4162 |
| ACG TCC ACC CCC AAT ACG GCC CAG CTG TTG CGC CAA AGC ATG CAC TCT<br>Thr Ser Thr Pro Asn Thr Ala Gln Leu Leu Arg Gln Ser Met His Ser<br>605     610     615     620 | 4210 |
| AAT AAC AAT ACG TCT CAT ACC TCC CCT AAT ACG CCG CCC GAG TCC GCC<br>Asn Asn Asn Thr Ser His Thr Ser Pro Asn Thr Pro Pro Glu Ser Ala<br>     625     630     635 | 4258 |
| CTG AGC AGC GCA GTT CCG TCC CGC CCG GCC AGT CCC GGG GGC AGC AAG<br>Leu Ser Ser Ala Val Pro Ser Arg Pro Ala Ser Pro Gly Gly Ser Lys<br>   640     645     650 | 4306 |
| AAC GGC GAC CAA GGC AGC AAC GGA CCG ACC ACC TGC ACG AAC TGC TTC<br>Asn Gly Asp Gln Gly Ser Asn Gly Pro Thr Thr Cys Thr Asn Cys Phe<br>655     660     665 | 4354 |

| | | |
|---|---|---|
| ACT CAA ACC ACT CCG CTG TGG CGT CGG AAC CCA GAG GGC CAG CCA CTG<br>Thr Gln Thr Thr Pro Leu Trp Arg Arg Asn Pro Glu Gly Gln Pro Leu<br>       670                             675                       680 | 4402 | |
| TGC AAT GCC TGC GGG TTG TTT TTG AAA TTG CAC GGT GTC GTG CGC CCT<br>Cys Asn Ala Cys Gly Leu Phe Leu Lys Leu His Gly Val Val Arg Pro<br>685                      690                         695                         700 | 4450 | |
| CTG TCC CTG AAA ACG GAC GTT ATC AAA AAG CGC AAC CGT AGC AGT GCC<br>Leu Ser Leu Lys Thr Asp Val Ile Lys Lys Arg Asn Arg Ser Ser Ala<br>                      705                       710                       715 | 4498 | |
| AAC AGC TTG GCG GTT GGG ACC TCC CGT GCG TCG AAG AAG ACA GCC CGC<br>Asn Ser Leu Ala Val Gly Thr Ser Arg Ala Ser Lys Lys Thr Ala Arg<br>       720                           725                      730 | 4546 | |
| AAG AAC TCG GTG CAG CAA GCA TCC GTC ACG ACT CCG ACA TCA AGC CGC<br>Lys Asn Ser Val Gln Gln Ala Ser Val Thr Thr Pro Thr Ser Ser Arg<br>                      735                       740                       745 | 4594 | |
| GCT CAG AAT GGG ACT TCC TTC GAA TCC CCG CCC GCC GGC TTT AGT GCT<br>Ala Gln Asn Gly Thr Ser Phe Glu Ser Pro Pro Ala Gly Phe Ser Ala<br>       750                           755                      760 | 4642 | |
| GCC GCG GGA CGG TCG AAT GGG GTG GTA CCC ATT GCC GCC GCT CCT CCG<br>Ala Ala Gly Arg Ser Asn Gly Val Val Pro Ile Ala Ala Ala Pro Pro<br>765                      770                         775                       780 | 4690 | |
| AAG GCA GCT CCC TCC GCA GCC GCC TCC CCT AGC ACG GGC CAG ACC CGC<br>Lys Ala Ala Pro Ser Ala Ala Ala Ser Pro Ser Thr Gly Gln Thr Arg<br>                      785                       790                       795 | 4738 | |
| AAC CCG ATC CAG GCT GCC CCG AAA CGT CAA CGA CGG CTG GAA AAG GCC<br>Asn Pro Ile Gln Ala Ala Pro Lys Arg Gln Arg Arg Leu Glu Lys Ala<br>                           800                       805                      810 | 4786 | |
| ACG GAG ATG GAA ACG GAC GAG GCT AAC AAG TCC GCG GGA GGC CGA TCC<br>Thr Glu Met Glu Thr Asp Glu Ala Asn Lys Ser Ala Gly Gly Arg Ser<br>                      815                       820                       825 | 4834 | |
| AAG GTG GTG CCT CTG GCA CCC GCC ATG CCA CCG GCA GCA GCC AAT CCG<br>Lys Val Val Pro Leu Ala Pro Ala Met Pro Pro Ala Ala Ala Asn Pro<br>830                      835                         840 | 4882 | |
| GCG AAC CAT AGT ATT GCC GGA GGC CAA GGG GCT AGT CAG GAA TGG GAG<br>Ala Asn His Ser Ile Ala Gly Gly Gln Gly Ala Ser Gln Glu Trp Glu<br>845                      850                       855                       860 | 4930 | |
| TGG TTG ACG ATG AGT CTGTAATGGC CGCGCTTACC TCTCTACTTC TCTACACTCG<br>Trp Leu Thr Met Ser Leu<br>                 865 | 4985 | |
| TTTCTTAATA TCTTTCTTGA ACCCCCCCTT ATATTTTCCC ACCGTTGATG CTACGCCATG | 5045 | |
| ACCGATAGAG ATGATGAATA CTGCAACCAA TGGAATCTCG CTAGACGAGA GGTGTTAGAT | 5105 | |
| GACGTGGCCC GCGATGCACT TAATGAGATA CGAGGAGGTG CAATGCGTTG GTTACGCTAG | 5165 | |
| TTTAATGGTA ACATGACGAG GGATATTCGC TCTGTTATTT CGGGCTTTGA TCTGTTTCAG | 5225 | |
| TCTGCGATTT AACAGCGACT GATCCTCTGC TGTGACAATA CACAGCTTGT CTTGTGGTTC | 5285 | |
| TGTTGTGGCT TTCTGTTTGT TTGGCTGATT TGATTTATGC TTGATACAAT CGCGTCTGTC | 5345 | |
| CGGACCCCGG CCTTTGTTTT GTTTTCAGTT CTGATTCTTC ACTGTTTCTG ATTCTCTTGT | 5405 | |
| TCATGTTTTT GATTTGTTCA AGGCTTGGGG CCGGGCAGAA GTGCGCATCT CTGCTTTGTG | 5465 | |
| TTTTCCGTCA CCGTGCATAG ACGCTGTATG TATATGCTAC AGCAAGATTC TACTTATCCA | 5525 | |
| GTCTGAGCCT GTATTCATTG AAGTGTAGCC AGCTGTCGAA TGAGCTTTTT AACGATATTG | 5585 | |
| TTTTGTTGAG TAGTCAACAA GTAGTATCTG TATATTCCGG AGTCTAAGTA AGACACTT | 5643 | |

(2) INFORMATION FOR SEQ ID NO: 6:

(i) SEQUENCE CHARACTERISTICS:
        (A) LENGTH: 866 amino acids
        (B) TYPE: amino acid (D) TOPOLOGY: linear (ii) MOLECULE TYPE: protein (xi) SEQUENCE DESCRIPTION: SEQ ID NO: 6:

```
Met Ser Gly Leu Thr Leu Gly Arg Gly Pro Gly Val Arg Pro Thr
 1               5                  10                  15

Gln Thr Ala Thr Phe Thr Thr His His Pro Ser Ala Asp Ala Asp Arg
             20                  25                  30

Ser Ser Asn Asn Leu Pro Pro Thr Ser Ser Gln Leu Ser Asp Asp Phe
         35                  40                  45

Ser Phe Gly Ser Pro Leu Ser Pro Ala Asp Ser Gln Ala His Asp Gly
     50                  55                  60

Leu Leu Gln Asp Ser Leu Phe Pro Glu Trp Gly Ser Gly Ala Pro Arg
 65                  70                  75                  80

Pro Gly Ile Asp Ser Pro Asp Glu Met Gln Arg Gln Asp Pro Leu Ala
                 85                  90                  95

Thr Gln Ile Trp Lys Leu Tyr Ser Arg Thr Lys Ala Gln Leu Pro Asn
             100                 105                 110

Gln Glu Arg Met Glu Asn Leu Thr Trp Arg Met Met Ala Met Ser Leu
         115                 120                 125

Lys Arg Lys Glu Arg Glu Arg Ala Gln Gln Ser Met Phe Pro Ala Arg
130                 135                 140

Arg Gly Ser Ala Gly Pro Ser Gly Ile Ala Gln Leu Arg Ile Ser Asp
145                 150                 155                 160

Pro Pro Val Ala Thr Gly Asn Pro Gln Ser Thr Asp Leu Thr Ala Asp
                 165                 170                 175

Pro Met Asn Leu Asp Asp Phe Ile Val Pro Phe Glu Ser Pro Ser Asp
             180                 185                 190

His Pro Ser Pro Ser Ala Val Lys Ile Ser Asp Ser Thr Ala Ser Ala
         195                 200                 205

Ala Ile Pro Ile Lys Ser Arg Lys Asp Gln Leu Arg Asp Ser Thr Pro
     210                 215                 220

Val Pro Ala Ser Phe His His Pro Ala Gln Asp Gln Arg Lys Asn Ser
225                 230                 235                 240

Glu Phe Gly Tyr Val Pro Arg Arg Val Arg Lys Thr Ser Ile Asp Glu
                 245                 250                 255

Arg Gln Phe Phe Ser Leu Gln Val Pro Thr Arg Lys Arg Pro Ala Glu
             260                 265                 270

Ser Ser Pro Gln Val Pro Pro Val Ser Asn Ser Met Leu Ala His Asp
         275                 280                 285

Pro Asp Leu Ala Ser Gly Val Pro Asp Tyr Ala Leu Asp Ala Pro Ser
     290                 295                 300

Ser Ala Phe Gly Phe His Gln Gly Asn His Pro Val Asn His His
305                 310                 315                 320

Asn His Thr Ser Pro Gly Ala Pro Phe Gly Leu Asp Thr Phe Gly Leu
                 325                 330                 335

Gly Asp Asp Pro Ile Leu Pro Ser Ala Gly Pro Tyr Gln Ser Gln Phe
             340                 345                 350

Thr Phe Ser Pro Ser Glu Ser Pro Met Ala Ser Gly His Pro Phe Ala
         355                 360                 365

Asn Leu Tyr Ser His Thr Pro Val Ala Ser Ser Leu Asn Ser Thr Asp
     370                 375                 380

Phe Phe Ser Pro Pro Pro Ser Gly Tyr Gln Ser Thr Ala Ser Thr Pro
385                 390                 395                 400
```

-continued

```
Gln Pro Thr Tyr Asp Gly Asp His Ser Val Tyr Phe Asp Met Pro Ser
                405                 410                 415

Gly Asp Ala Arg Thr Gln Arg Arg Ile Pro Asn Tyr Ile Ser His Arg
            420                 425                 430

Ser Asn Leu Ser Ala Ser Leu Gln Pro Arg Tyr Met Phe Asn Gln Asn
        435                 440                 445

Asn His Glu Gln Ala Ser Ser Thr Val His Ser Pro Ser Tyr Pro
    450                 455                 460

Ile Pro Gln Pro Gln His Val Asp Pro Thr Gln Val Leu Asn Ala Thr
465                 470                 475                 480

Asn Tyr Ser Thr Gly Asn Ser His His Thr Gly Ala Met Phe Ser Phe
                485                 490                 495

Gly Ala Asp Ser Asp Asn Glu Asp Asp Asp Gly His Gln Leu Ser Glu
            500                 505                 510

Arg Ala Gly Leu Ala Met Pro Thr Glu Tyr Gly Asp Glu Asp Gly Phe
        515                 520                 525

Ser Ser Gly Met Gln Trp Asp Gly Gln Phe Pro Gly Ser Phe His Ser
    530                 535                 540

Leu Pro Gly Phe Gly Pro Gln His Arg Lys His Val Thr Ile Gly Ser
545                 550                 555                 560

Thr Asp Met Met Asp Thr Pro Glu Glu Trp Asn His Gly Gly Ser Leu
                565                 570                 575

Gly Arg Thr His Gly Ser Val Ala Ser Val Ser Glu Val Arg Asn Arg
            580                 585                 590

Glu Gln Asp Pro Arg Arg Gln Lys Ile Ala Arg Thr Thr Ser Thr Pro
        595                 600                 605

Asn Thr Ala Gln Leu Leu Arg Gln Ser Met His Ser Asn Asn Asn Thr
    610                 615                 620

Ser His Thr Ser Pro Asn Thr Pro Pro Glu Ser Ala Leu Ser Ser Ala
625                 630                 635                 640

Val Pro Ser Arg Pro Ala Ser Pro Gly Gly Ser Lys Asn Gly Asp Gln
                645                 650                 655

Gly Ser Asn Gly Pro Thr Thr Cys Thr Asn Cys Phe Thr Gln Thr Thr
            660                 665                 670

Pro Leu Trp Arg Arg Asn Pro Glu Gly Gln Pro Leu Cys Asn Ala Cys
        675                 680                 685

Gly Leu Phe Leu Lys Leu His Gly Val Val Arg Pro Leu Ser Leu Lys
    690                 695                 700

Thr Asp Val Ile Lys Lys Arg Asn Arg Ser Ser Ala Asn Ser Leu Ala
705                 710                 715                 720

Val Gly Thr Ser Arg Ala Ser Lys Lys Thr Ala Arg Lys Asn Ser Val
                725                 730                 735

Gln Gln Ala Ser Val Thr Thr Pro Thr Ser Ser Arg Ala Gln Asn Gly
            740                 745                 750

Thr Ser Phe Glu Ser Pro Pro Ala Gly Phe Ser Ala Ala Ala Gly Arg
        755                 760                 765

Ser Asn Gly Val Val Pro Ile Ala Ala Ala Pro Pro Lys Ala Ala Pro
    770                 775                 780

Ser Ala Ala Ala Ser Pro Ser Thr Gly Gln Thr Arg Asn Pro Ile Gln
785                 790                 795                 800

Ala Ala Pro Lys Arg Gln Arg Leu Glu Lys Ala Thr Glu Met Glu
                805                 810                 815

Thr Asp Glu Ala Asn Lys Ser Ala Gly Gly Arg Ser Lys Val Val Pro
```

```
                          820                 825                 830
Leu Ala Pro Ala Met Pro Pro Ala Ala Ala Asn Pro Ala Asn His Ser
                835                 840                 845

Ile Ala Gly Gly Gln Gly Ala Ser Gln Glu Trp Glu Trp Leu Thr Met
    850                 855                 860

Ser Leu
865
```

(2) INFORMATION FOR SEQ ID NO: 7:

(i) SEQUENCE CHARACTERISTICS:
        (A) LENGTH: 27 nucleotides
        (B) TYPE: nucleic acid
        (C) STRANDEDNESS: single
        (D) TOPOLOGY: linear (ii) MOLECULE TYPE: DNA Primer 19819

(iii) HYPOTHETICAL: YES (iii) ANTI-SENSE: NO (xi) SEQUENCE DESCRIPTION: SEQ ID NO: 7:

GAAGATCTGC GCGGATGTAC ATTGTAG                                            27

(2) INFORMATION FOR SEQ ID NO: 8:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA Primer 19821

(iii) HYPOTHETICAL: YES (iii) ANTI-SENSE: NO (xi) SEQUENCE DESCRIPTION: SEQ ID NO: 8:

TTAGTCAGAA ATTCGTCCCG                                                      20

(2) INFORMATION FOR SEQ ID NO: 9:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: DNA Primer 19820

(iii) HYPOTHETICAL: YES (iii) ANTI-SENSE: NO (xi) SEQUENCE DESCRIPTION: SEQ ID NO: 9:

CCCAAGCTTC ATGCTCGACC AGGGCCTCCT                                     30

(2) INFORMATION FOR SEQ ID NO: 10:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (ii) MOLECULE TYPE: DNA Primer 19818

(iii) HYPOTHETICAL: YES

-continued (iii) ANTI-SENSE: NO (xi) SEQUENCE DESCRIPTION: SEQ ID NO: 10:

GGTCTGTGTT AACCAAAGAA C          21

(2) INFORMATION FOR SEQ ID NO: 11:

(i) SEQUENCE CHARACTERISTICS:
        (A) LENGTH: 14 nucleotides
        (B) TYPE: nucleic acid
        (C) STRANDEDNESS: single
        (D) TOPOLOGY: linear (ii) MOLECULE TYPE: DNA Primer 8681

(iii) HYPOTHETICAL: YES (iii) ANTI-SENSE: NO (xi) SEQUENCE DESCRIPTION: SEQ ID NO: 11:

GATCCACCAT GAAG          14

(2) INFORMATION FOR SEQ ID NO: 12:

(i) SEQUENCE CHARACTERISTICS:
        (A) LENGTH: 14 nucleotides
        (B) TYPE: nucleic acid
        (C) STRANDEDNESS: single
        (D) TOPOLOGY: linear (ii) MOLECULE TYPE: DNA Primer 8747

(iii) HYPOTHETICAL: YES (iii) ANTI-SENSE: NO (xi) SEQUENCE DESCRIPTION: SEQ ID NO: 12:

GTGGTACTTC AGCT          14

FUNGUS WHEREIN THE AREA, PEPC AND/ OR PEPE GENES HAVE BEEN INACTIVATED

CROSS-REFERENCE TO RELATED APPLICATIONS

This application is a continuation application of PCT/DK96/00528 filed Dec. 16, 1996 and claims priority under 35 U.S.C. 119 of Danish application 1428/95 filed Dec. 15, 1995, the contents of which are fully incorporated herein by reference.

FIELD OF THE INVENTION

The present invention relates to fungi, which do not produce proteases. The fungi of the invention are useful as hosts for the production of proteins susceptible to proteolytic degradation by the proteases usually produced, and the invention consequently encompasses processes for the production of proteins of interest in high yields by using the fungi of the invention. The invention also comprises methods for producing such fungi and DNA constructs to be used in these methods.

BACKGROUND OF THE INVENTION

Fungi, and especially filamentous fungi, are widely used commercially because of their ability to secrete remarkably high levels of proteins Among the filamentous fungi species belonging to the genus Aspergillus have a long history of commercial use for the production of endogenous and lately also heterologous proteins.

One disadvantage with most microorganisms used for the production of proteins is the inherent production of proteases which may subject a protein product of interest to degradation due to proteolysis.

Various ways of avoiding this have been envisaged. Among other solutions it has been suggested to delete or disrupt the genes encoding the various proteases. Unfortunately, the fungi produce a high number of proteases making such a solution more or less unrealistic.

A need is therefore persisting for strains of filamentous fungi exhibiting no or very low levels of protease production.

For a number of years it has been known that the regulatory gene areA which mediates nitrogen metabolite repression in *A. nidulans* influences the production of extracellular proteases (Arst & Cove, *molec. gen. Genet.* 126, (1973) 111–141).

The areA gene from *A. nidulans* has been cloned (Caddick et al., *EMBO Journal* 5, (1986) 1087–1090) and various modifications made to it to evaluate functions of different regions in the activator protein encoded by this gene (Stankovitch et al. *Mol. Microbiol.* 7, (1993) 81–87). Furthermore the gene coding the corresponding function in *A. fumigatus* apparently has been cloned recently (Hensel et al. 2nd European Conference on Fungal Genetics, Apr. 28 to May 1, 1994, Book of Abstracts, E11).

From the literature a single use is also known of a strain of *A. nidulans* of genotype argB areA1 as a host for the production of t-PA (Upshall et al. *Biotechnology* 5, (1987) 1301–1304). In this example only the argB genotype is used as a selection marker through its arginine prototrophy, while the areA genotype is simply a coincidence.

International Patent Publication No. WO 95/35385 discloses the deletion of the areA gene as a means for reducing the protease level in filamentous fungi.

Apart from the extracellular proteases, fungi also produce a number of intracellular proteases (also called endoplasmic).

Among these a serine protease of the subtilisin type produced by *A. niger* and designated PepC has been described, the gene expressing it cloned, and a deletion mutant described in EP 574 347 and in Frederick et al., *Gene*, 125 57–64 (1993)

A further such protease of the aspartic type designated PepE has been disclosed in Jarai et al., *Gene*, 145 171–178 (1994). the article discloses the cloning and characterisation of the pepE gene and speculates about the regulation of the pepE and pepC genes.

The present invention has as an object the alleviation of the need for protease free filamentous fungi.

SUMMARY OF THE INVENTION

The present invention consequently relates to fungi, wherein the areA, pepC, and/or pepE genes by recombinant DNA technology have been modified such that they cannot be expressed in a way providing for a functional AreA activator and functional PepC and/or PepE proteases.

The invention furthermore relates to methods for producing such fungi, obtained by deletion of the areA, pepC, and/or pepE genes.

This may be obtained through a method comprising i) cloning of the areA, pepC, and/or pepE genes from a fungus of interest, ii) producing DNA constructs each comprising one among the areA gene, the pepC gene, and the pepE gene, wherein an internal part has been substituted, deleted, or extra DNA has been inserted, iii) transforming said fungus with the constructs, and iv) isolating transformants which are areA$^-$, pepC$^-$, and/or pepE$^-$.

The information obtained from the above mentioned cloning of the areA, pepC, and/or pepE genes may also be used in connection with the well-known anti-sense technology, to construct an expression plasmid giving rise to synthesis of a RNA molecules complementary to the mRNA transcribed from the areA, pepC, and/or pepE genes, and to transform the fungus of interest therewith.

The invention furthermore relates to DNA constructs intended for use in the above mentioned methods.

Furthermore the invention relates to methods of producing a desired protein or gene product, especially secreted proteins, whereby a fungal host modified and optionally transformed with a DNA construct comprising at least a DNA sequence coding for the protein or gene product of interest, is cultivated in a suitable growth medium at appropriate conditions and the desired gene product is recovered and purified.

When working with the invention it was surprisingly found that the fungi of the invention produces such secreted proteins in a much improved yield.

It was also surprisingly found that the only nitrogen source capable of providing good growth of the *A. oryzae* areA$^-$ strains was glutamine.

The invention furthermore relates to protein products produced by the above methods.

Also the invention relates to a DNA sequence coding for the pepC gene from *A. oryzae* (SEQ ID No. 1) or functional alleles thereof.

The invention also covers a PepC protease from *A. oryzae* (SEQ ID No. 2), and processes for the production of the PepC protease comprising transforming a suitable host with a DNA construct comprising a DNA sequence coding for the PepC protease, selecting a transformant capable of producing said PepC protease, cultivating said transformant in an appropriate growth medium and recovering said PepC protease from said culture.

Furthermore the invention relates to a DNA sequence coding for the pepE gene from A. oryzae (SEQ ID No. 3) or functional alleles thereof.

Also, the invention relates to a PepE protease from A. oryzae (SEQ ID No. 4), and processes for the production of the PepE protease comprising transforming a suitable host with a DNA construct comprising a DNA sequence coding therefore, selecting a transformant capable of producing said PepE protease, cultivating said transformant in an appropriate growth medium and recovering said PepE protease from said culture.

According to these aspects said host is preferably a fungus, according to the invention, especially A. oryzae, and wherein said DNA construct provides for an extra copy of the gene encoding either said PepC or PepE protease.

BRIEF DESCRIPTION OF THE DRAWING

The invention is described in further detail in the following parts of the specification with reference to the Examples and the drawing, wherein.

DEFINITIONS

Figure 1:
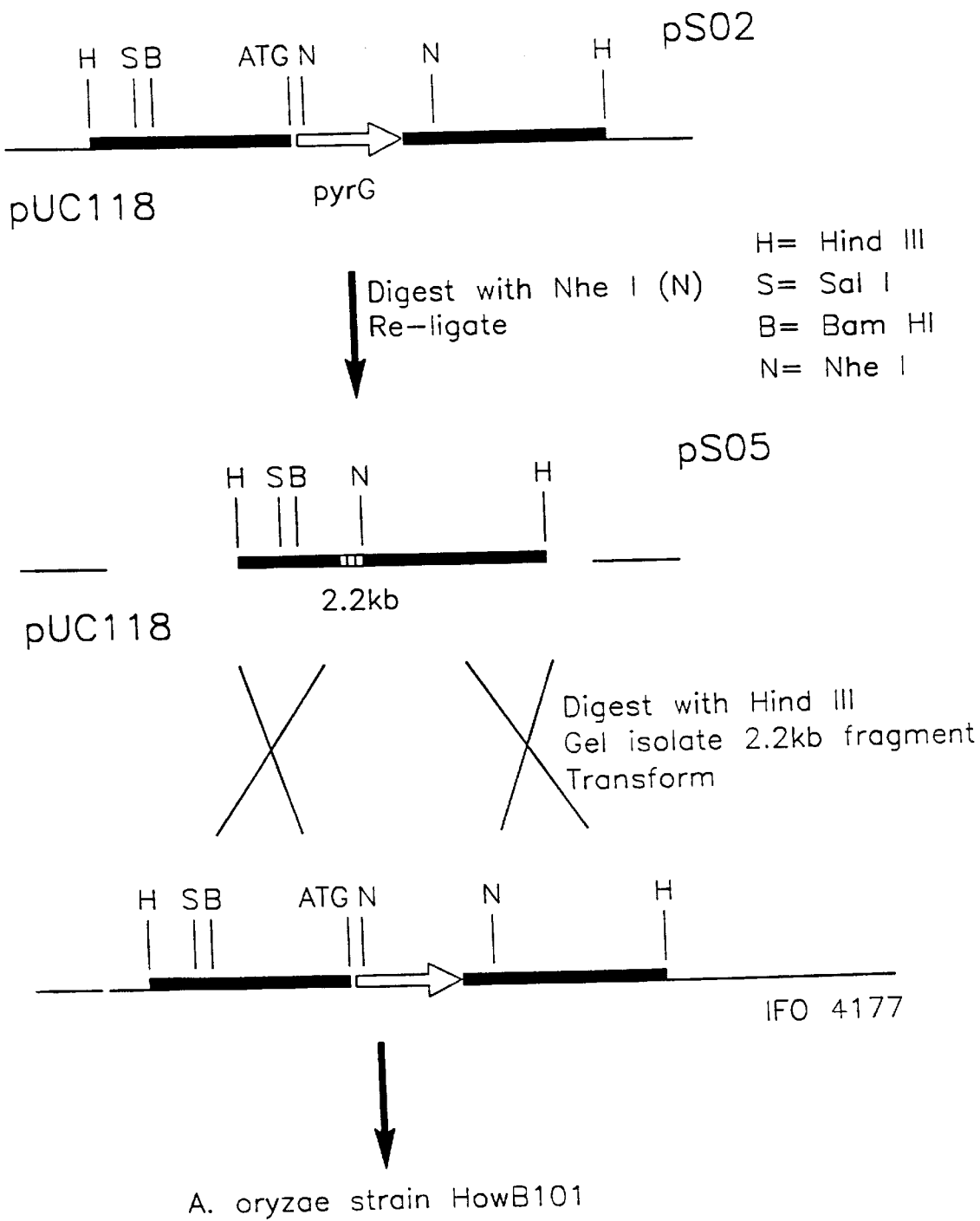
FIG. 1 shows the steps involved in the construction of HowB101.

In the present specification the following definitions are used:

The expression areAD means a strain in which the areA gene is deleted. Similar notations are used for strains, wherein the pepC, and/or pepE genes are deleted.

The expression areA$^-$ means a strain which does not produce a functional AreA activator. The term "loss of function" is also often used for this. Similar notations used for strains, which do not produce functional PepC, and/or PepE protease(s).

The expression "anti-sense technology" describes methods such as disclosed in U.S. Pat. No. 5,190,931.

DETAILED DESCRIPTION OF THE INVENTION

As indicated the present invention relates in its first aspect to fungi, wherein the areA gene by recombinant DNA technology has been modified in a way by which it cannot be expressed in a way providing for a functional AreA activator, and wherein the genes encoding for the extracellular proteases PepC and/or PepE has been inactivated in a manner whereby they are not expressed to produce functional proteases.

This object may specifically be obtained by deletion or disruption of the areA, pepC, and/or pepE genes.

The cloning of the areA, pepC, and/or pepE genes are described in the Examples.

AreA homologs from other fungi could be cloned either by cross hybridization with one of the already known genes or by complementation of areA mutants; e.g. A. nidulans areA-18 or the A. oryzae areA deleted strain described in this application.

Methods for deleting or disrupting a gene are specifically described in WO 90/00192 (Genencor).

Methods for substituting DNA in a gene are also generally known, and can be accomplished by substituting one or more continuous parts of the gene, but it may also be obtained by site directed mutagenesis generating a DNA sequence encoding a AreA activator variant that is not functional.

Another method by which such an object may be obtained is by using anti-sense technology.

The anti-sense technology and how to employ it is described in detail in the aforementioned U.S. Pat. No. 5,190,931 (University of New York).

A further method of obtaining said inactivation is by inserting extra DNA internally in the areA gene, thereby giving rise to the expression of a dysfunctional activator protein.

In connection with this method information provided by the cloning can be used to make DNA constructs that can be integrated into the areA gene, and even replace it with another gene, such as the pyrG gene.

A further method of avoiding the presence of the areA activator is by interfering with the regulation of the expression signals regulating the expression of the areA gene itself.

The principles described above apply equally to the pepC, and/or pepE genes.

According to the invention the fungus preferably belongs to a genus selected from the group comprising Aspergillus, Trichoderma, Humicola, Candida, Acremonium, Fusarium, and Penicillium.

Among these genera species selected from the group comprising A. oryzae, A. niger, A. awamori, A. phoenicis, A. japonicus, A. foetidus, A. nidulans, T. reesei, T. harzianum, H. insolens, H. lanuginosa, F. graminearum, F. solani, P. chrysogenum, and others are preferred.

As indicated the invention also is meant to encompass the method for producing the fungi of the first aspect of the invention, and wherein said inactivation has been obtained by deletion of the areA, pepC, and/or pepE genes, which method comprises i) cloning of the areA, pepC, and/or pepE genes from a fungus of interest,
ii) producing DNA constructs each comprising one among the areA gene, the pepC gene, and/or the pepE gene, wherein an internal part has been substituted, deleted, or extra DNA has been inserted,
iii) transforming said fungus with the constructs, and
iv) isolating transformants which are areA$^-$, pepC$^-$, and/or pepE$^-$.

Since it is believed that the maturation of the PepC protease is controlled by the PepE protease the invention also comprises a method for producing a fungus of the invention, wherein said inactivation has been obtained by deletion of the areA and pepE genes, which method comprises i) cloning of the areA and pepE genes from a fungus of interest,
ii) producing DNA constructs each comprising one among the areA gene and the pepE gene, wherein an internal part has been substituted, deleted, or extra DNA has been inserted,
iii) transforming said fungus with the constructs, and
iv) isolating transformants which are areA⁻, and pepE⁻.

Also included is the method for producing the fungi, wherein the inactivation has been obtained by using anti-sense technology. Such a method comprising i) construction of expression plasmids, each of which give rise to synthesis of an RNA molecule complementary to the mRNA transcribed from the areA gene, the pepC gene, and/or the pepE gene,
ii) transformation of the host fungus with said expression plasmids and a suitable marker, either on separate plasmids or on the same plasmid,
iii) selection of transformants using said marker, and
iv) screening selected transformants for strains exhibiting a reduction in the synthesis of the AreA, PepC, and/or PepE products.

A further aspect of the invention is meant to comprise DNA constructs for use in the above mentioned methods.

In respect of the former method said DNA constructs may comprise the areA, pepC, and/or pepE genes, wherein an internal part has been substituted, deleted, or extra DNA has been inserted.

At least one of the DNA constructs may furthermore also comprise DNA sequences encoding a protein product of interest, such as those mentioned later.

In respect of the latter anti-sense method the DNA constructs may comprise inverted DNA sequence of the areA, pepC, and/or pepE genes connected to a functional promoter, whereby the mRNAs are at least partially complementary to mRNAs produced from the areA, pepC, and/or pepE genes.

A further aspect of the invention relates to a process for the production of a desired gene product, preferably a secreted gene product, whereby a fungus according to the invention is cultivated in a suitable growth medium at appropriate conditions and the desired gene product is recovered and purified.

In the case of a gene product expressed by a heterologous gene the DNA sequence coding for the desired gene product may be a part of the DNA construct used for producing said fungus.

Normally, however, a separate transformation of the fungus of the invention is performed in order to make the fungus capable of producing the desired product.

Methods for transforming fungi are well known in the art, cf. e.g. EP 0 184 438 A2 (Gist-Brocades N.V.) and EP publication No. 0 98 993 (Novo Nordisk A/S).

For indigenous products this is of course not necessary, but in order to increase the production it may be an advantage to provide for multiple copies of the gene encoding the protein of interest to be incorporated into the host.

The desired gene product is generally a peptide or protein, preferably an enzyme.

Among enzymes it is preferably selected from the group comprising proteases, such as trypsin and chymosin; lipases, cutinases, cellulases, xylanases, laccases, pectinases, etc.

Another type of desired gene product is generally a therapeutically active peptide or protein.

Among the therapeutically active peptide or protein the protein preferably is selected from the group comprising insulin, growth hormone, glucagon, somatostatin, interferons, PDGF, factor VII, factor VIII, urokinase, t-PA, CSF, lactoferrin, TPO etc.

A further aspect of the invention relates to the DNA sequences coding for the pepC gene from A. oryzae (SEQ ID No. 1), the pepE gene from A. oryzae (SEQ ID No. 3) or functional alleles thereof. Also encompassed by the invention are the corresponding PepC and PepE proteases and their production, preferably by recombinant means.

In this aspect the invention relates to processes for the production of the PepC protease or PepE protease from A. oryzae comprising transforming a suitable host with a DNA construct comprising a DNA sequence encoding the protease of interest, selecting a transformant capable of producing the protease, cultivating the transformant in an appropriate growth medium and recovering the PepC or PepE protease from the culture.

The host used in such a process is preferably a host according to the above mentioned aspects of the invention In certain embodiments of the process for producing the PepC or PepE protease the host is A. oryzae. In that case it is preferred that the DNA construct comprising a DNA sequence coding for the protease, provides for an extra copy of the gene already present in the host.

The DNA construct comprising the DNA sequence encoding the protease will normally also comprise regulatory elements in order to provide for proper expression and processing of the protease in the host.

The invention is explained in further detail in the Examples given below. These should, however, not in any way be construed as limiting the scope of the invention as defined in the appended claims.

EXAMPLES

Materials and Methods

Strains

A. oryzae, IFO4177: available from Institute for Fermentation, Osaka; 17–25 Juso Hammachi 2-Chome Yodogawa-Ku, Osaka, Japan.

ToC913: The construction of this strain is described in the Examples.

Genes areA: This gene codes for a regulatory protein controlling nitrogen catabolism.

pepC: This gene codes for a serine protease of the subtilisin type pepE: This gene codes for an aspartic protease.

pyrG: This gene codes for orotidine-S'-phosphate decarboxylase, an enzyme involved in the biosynthesis of uridine.

bar: This gene was originally isolated from *Streptomyces hygroscopicus* and codes for phosphinothricin acetyltransferase. The enzyme modifies phosphinothricin (=glufosinate) and thereby inactivates this compound which is toxic to bacteria, fungi and plants.

Plasmids pUC118: Viera and Mesing *J. Meth. Enzymol.* 1987 153 3–11 pSO2: The construction of this plasmid is described in the Examples.

pJers4: A 2.0 kb subclone of pSO2 in pUC118. pJers4 contains a functional *A. oryzae* pyrG gene.

pS05: The construction of this plasmid from pSO2 is described in the Examples.

pToC56: The construction of this plasmid is described in EP publication No. 0 98 993.

pToC68: The construction of this plasmid is described in WO 91/17243.

pToC90: A subclone of p3SR2, harboring the amdS gene from *Aspergillus nidulans* as a 2.7 kb XbaI fragment [Corrick et al., GENE 1987 53 63–71], on a PUC19 vector[Yannisch-Perron et al., GENE 1985 33 103–119], prepared as described in WO 91/17243.

pToC266: The construction of this plasmid is described in the Examples.

pToC299: The construction of this plasmid is described in the Examples.

pToC338: The construction of this plasmid is described in the Examples.

pMT1606: The construction of this plasmid from pBP1T (B. Straubinger et al. Fungal Genetics Newsletter 39(1992): 82–83) and p775 (EP publication No. 0 98 993) is described in the Examples.

p775: The construction of this plasmid is described in EP publication No. 0 98 993.

p777: The construction of this plasmid is described in EP publication No. 0 98 993.

pHW470: The construction of this plasmid is described in the Examples.

Example 1

Cloning and Deletion of the *A. oryzae* pepE Gene.

The *A. oryzae* pepE gene was cloned by cross-hybridization with the *A. niger* gene. A partial *A. niger* gene was obtained as a 700 bp PCR fragment from a PCR reaction with *A. niger* chromosomal DNA and pepE specific primers made according to the pepE sequence published by G. Jarai et al, Gene 145 (1994) 171–178. The fragment was shown to contain pepE sequences by DNA sequencing. It hybridizes to *A. oryzae* chromosomal DNA under stringent conditions and Southern analysis showed that *A. oryzae* contains a single pepE like gene.

The pepE gene was deleted both by the gene replacement method and the two step gene replacement method (G. May in "Applied Molecular Genetics of Filamentous Fungi" (1992) pp. 1–25. Eds. J. R. Kinghorn and G. Turner; Blackie Academic and Professional). As marker was used the *A. oryzae* pyrG gene, the *A. oryzae* strain was a pyrG- strain made by deletion of the pyrG gene.

Cloning of the *A. oryzae* pepE Gene

A cosmid library of *Aspergillus oryzae* was constructed essentially according to the instruction from the supplier (Stratagene) of the "SuperCos1 cosmid vector kit".

Genomic DNA of *A. oryzae* IFO4177 was prepared from protoplasts made by standard procedures (Christensen, T., et. al., Biotechnology 6 (1988) 1419–1422). After isolation of the protoplasts they were pelleted by centrifugation at 2500 rpm for 5 minutes in a Labofuge T (Heto), the pellet was suspended in 10 mM NaCl, 20 mM Tris-HCl (pH 8.0), 1 mM EDTA, 100 µg/ml proteinase K and 0.5% SDS as stated in the manual from the Supercos 1 cosmid vector kit and the rest of the DNA preparation was done according to the kit's instructions. The size of the genomic DNA was analysed by electrophoresis using the CHEF-gel apparatus from Biorad. A 1% agarose gel was run for 20 hours at 200 volt with a 10–50 second pulse. The gel was stained by etidium bromide and photographed. The DNA was 50->100 kb in size. The DNA was partially restricted by Sau3A. The size of the restricted DNA was 20–50 kb determined by the same type of CHEF-gel analysis as above. The CsCl gradient banded SuperCos1 vector was prepared according to the manual. Ligation and packaging was likewise done as described. After titration of the library all of the packaging mix from one ligation and packaging was transfected into the host cells XL1-Blue MR and plated on 50 µg/ml ampicillin LB plates. Approximately 3800 colonies were obtained. Cosmid preparation from 10 colonies showed that they all had inserts of the expected size. The colonies were picked individually and inoculated in microtiter plate wells with 100 µl LB (100 µg/ml ampicillin) and incubated at 37° C. over night. 100 µl of 50% glycerol was added to each well and the whole library was frozen at −80° C. A total of 3822 colonies were stored. This represents the *A. oryzae* genome apr. 4.4 times.

The individually frozen colonies in the library were inoculated onto LB-plates (1000µg/ml ampicillin) by using a multipin device with 6 times 8 pins fitting into half a microtiter dish. Plates were made containing colonies from all clones in the library. The plates were incubated at 37° C. over night. Sterilized Whatman 540 filters cut to the size of a petri dish were placed upon the colonies which were incubated for two more hours at 37° C. The filters were transferred to LB plates containing 200 µg/ml of chloramphenicol and the plates were incubated over night at 37° C. The next day the filters were washed twice in 0.5 M NaOH for 5 minutes, then twice in 0.5 M Tris-HCl (pH=7.4) for 5 minutes and then twice in 2×SSC for 5 minutes. The filters were wet with ethanol and air-dried.

The filters were hybridized with a 0.7 kb $^{32}$P labelled PCR fragment containing part of the pepE gene from *A. niger* . The PCR fragment was obtained by running PCR on chromosomal DNA from *A. niger* with two primer 700 bp apart in the DNA sequence. The hybridization was carried out for 16 hours at 65° C. in 10×Denhart, 5×SSC, 0.02 M EDTA, 1% SDS, 0.15 mg/ml polyA and 0.05 mg/ml yeast tRNA. After hybridization the filters were washed in 2×SSC, 0.1% SDS at 45° C. twice and placed on X-ray films. 5 colonies hybridized with the probe, 4 of them were subsequently shown to contain the *A. oryzae* pepE gene by Southern analysis of the isolated cosmid DNA, using the same probe. Three of the cosmids were identical, thus two different cosmid clones containing pepE were isolated, they were called 7C7 and 33C1, names referring to their position in the stored library. Two overlapping fragments, a 4.3 kb EcoRI fragment (pToC299) and a 2.4 kb HindIII (pToC301) fragment, were subcloned and partially sequenced. SEQ. ID No. 1 shows the DNA sequence and the deduced aa sequence for the protease. The gene shows strong homology to the *A. niger* gene.

Cloning of the *A. oryzae* PyrG Gene

The *A. oryzae* pyrG gene was cloned by cross hybridization with the *A. niger* pyrG gene (W. van Hartingsveldt et al., Mol. Gen. Genet 206: 71–75 (1987)). A lambda library of partial SauIIIA digested *A. oryzae* IFO04177 DNA was probed at low stringency with a 1 kb DNA fragment from the *A. niger* pyrG gene. A 3.8 kb HindIII fragment from a positive clone was subcloned into a pUC118 vector. The resultant plasmid, pSO2, was shown to contain the pyrG gene by complementation of an *A. niger* pyrG⁻ mutant.

Construction of an *A. oryzae* pyrG Minus Strain

A pyrG deletion plasmid, pSO5, containing about 1 kb of pyrG flanking sequences on each end was constructed from the plasmid pSO2. *A. oryzae* IFO04177 was transformed with this construct and transformants were selected by resistance to 5-fluoro-orotic acid (FOA), a phenotype characteristic of pyrG mutants. One transformant, HowB101, was shown by Southern analysis to have the expected deletion at the pyrG locus. Being a pyrG mutant HowB101 requires uridine for growth. HowB101 can be transformed with the wt pyrG gene by selection for ability to grow without uridine.

The steps involved in the construction of HowB101 are illustrated in FIG. 1.

Deletion of the pepE Gene in *A. oryzae*. by the Gene Replacement Method

A plasmid, pToC345, designed to replace the pepE gene with the pyrG gene, was constructed.

Two PCR reactions were run with pToC299 as template; the first primer set was:

```
19819 GAAGATCTGCGCGGATGTACATTGTAG

19821 TTAGTCAGAAATTCGTCCCG
```

The second was:

```
19820 CCCAAGCTTCATGCTCGACCAGGGCCTCCT

19818 GGTCTGTGTTAACCAAAGAAC
```

Figure 2:
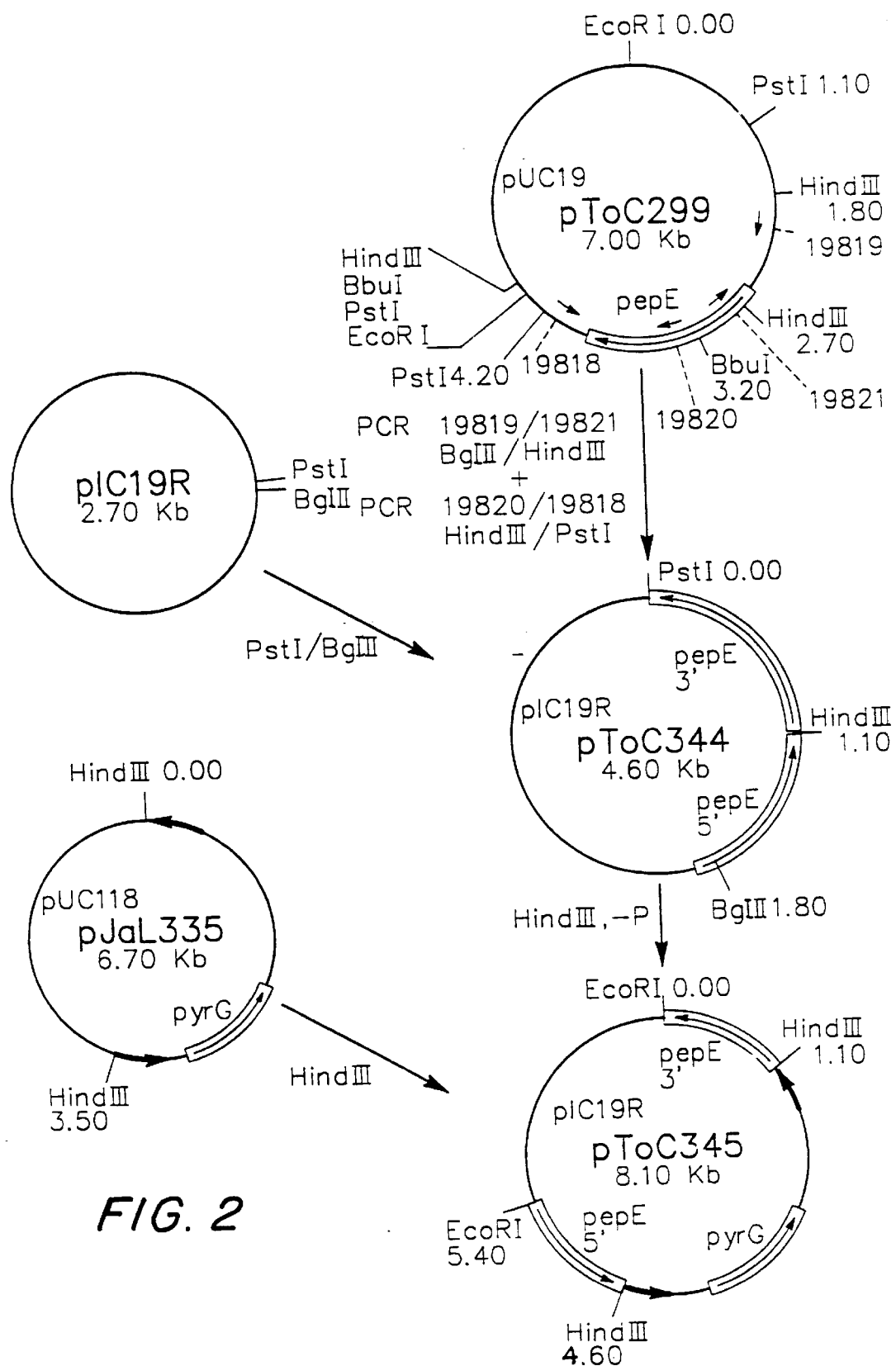
FIG. 2 shows the construction of pToC345.

The appr. 800 bp fragment obtained with 19819/19821 was cut with BglII/HindIII and cloned together with the 1.1 kb fragment obtained with 19820/19818 and cut with HindIII/PstI into BglII/PstI cut pIC19R (J. L. Marsh et al, Gene 32 (1984) 481–484). The resulting plasmid was cut at the unique HindIII site, dephosphorylated and the 3.5 kb pyrG containing fragment from pJaL335 (described in Example 2) was inserted. The construction of pToC345 is illustrated in FIG. 2.

HowB101 was transformed with EcoRI cut pToC345 using standard procedures and transformants were selected by their ability to grow without the addition of uridine. 100 formants were reisolated once through conidiospores. Spores were picked from single colonies on the reisolation plates and suspended in 100 ml of water with 0.01% Trition X-100. 1 ml spore suspension from each transformant and from IFO04177, which was included as a control strain, were spotted on two Whatmann 540 filters placed on top of each their YPD plate. The plates were incubated at 30° C. for 18 hours. The filters were removed from the plates and placed in 20% SDS for two hours at room temperature. They were then bakes for 3 minutes in a 600W micro-wawe oven. The filters were then washed for 5 minutes in 10% SDS, 2 times 5 minutes in 0.5M NaOH, 1.5M NaCl, one time 5 minutes in 0.5MTris-HCl pH=7.5, 1.5M NaCl and one time 5 minutes in 20×SSC and air dried. The two sets of filters were hybridized by standard procedures with each their $^{32}$P-labelled probe. One set was hybridized with a 600 bp BbuI/HindIII fragment from pToC299 containing the part of the pepE gene that was attempted to be deleted. The other set of filters was hybridized with a DNA fragment from the *A. oryzae* tpi gene. Any gene present in one copy, but pepE could be used since this is a control of the amount of DNA bound to the filters.

After hybridization the filters were washed with 0.1×SSC, 0.1% SDS at 65° C. and the radioactivity bound to the filters were visualized by a PhospoImager. 13 of the transformants were picked for further analysis because they showed little hybridization to the pepE probe compared to the hybridization to the control probe. Chromosomal DNA was prepared by standard procedures and a Southern blot of the EcoRI restricted DNA was hybridized with a $^{32}$ P-labelled 1.1 kb BbuI fragment from pToC299 containing the 3' part of the pepE gene which was not to be deleted. In the wt strain a 4.3 kb fragment should hybridize to the probe, in a correct replacement strain the 4.3 kb fragment should be replaced by a 7.2 kb fragment. Two of the transformants looked correct, one had no hybridizing bands at all and most had the wt band plus maybe one other band, indicating integration of the transforming DNA at a non-homologous locus.

In order to isolate a pyrG$^-$ derivative of the pepE deleted strain 10$^7$ conidiospores were spread on FOA containing plates and resistant colonies were selected. The FOA resistant colonies were reisolated, DNA was prepared and Southern analysis was performed to identify the strains in which the pyrG gene was lost via recombination between the repeat sequences flanking the gene in pToC345.

Figure 3:
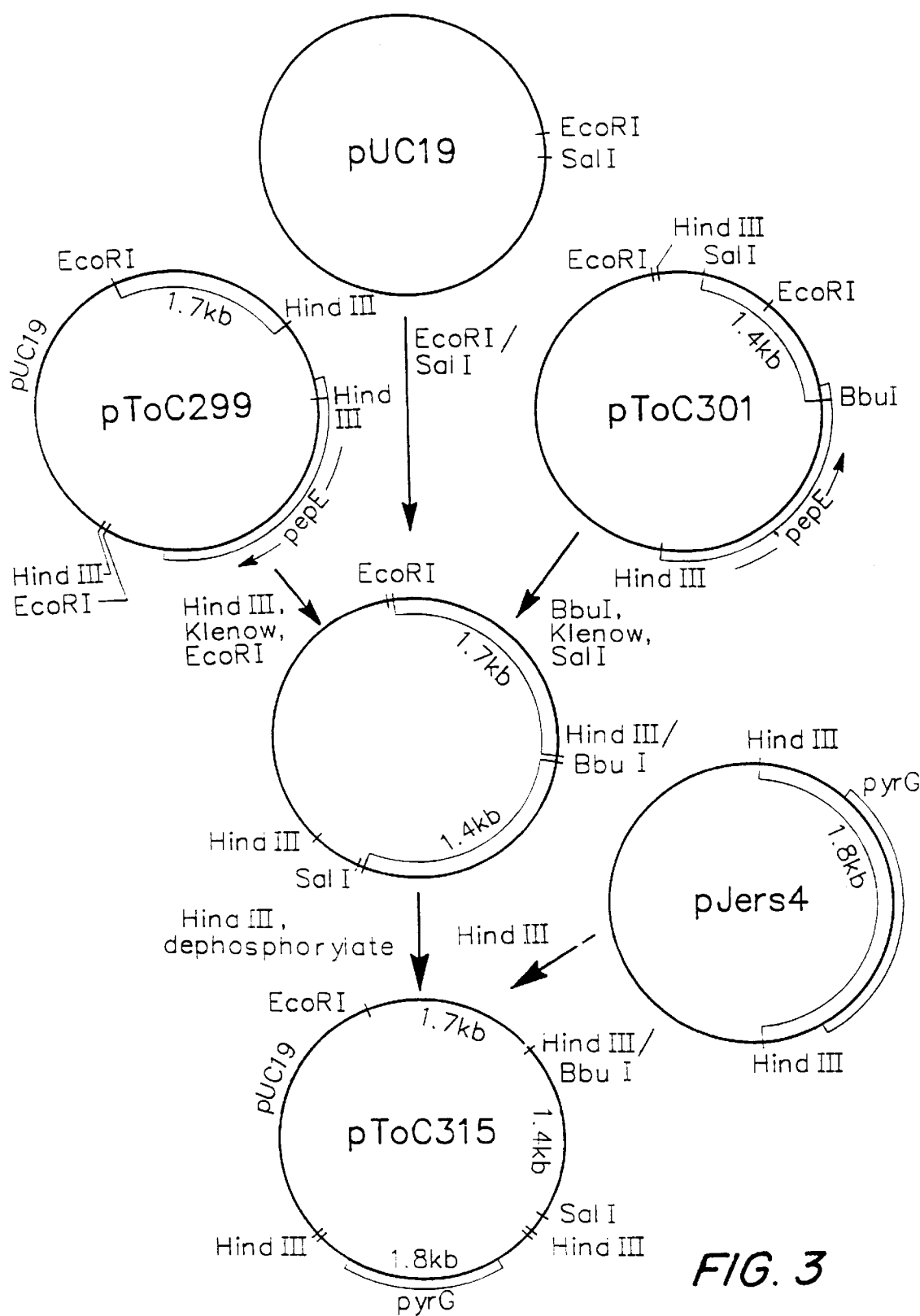
FIG. 3 shows the steps involved in the construction of pToC315.

Deletion of the pepE Gene in *A. oryzae* by the Two Step Gene Replacement Method A plasmid, pToC315, designed for a two step gene deletion of the pepE gene was constructed. A 1.6 kb EcoRI/HindIII (the HindIII site was blunt ended by treatment with the Klenow fragment of DNA polymerase) from pToC299 containing sequences upstream from the pepE gene was cloned together with a 1.4 kb SalI/BbuI (the BbuI fragment was blunt ended) containing the 3' end of the pepE gene into the EcoRI/SalI cut vector pUC19. The resulting plasmid was cut at the unique HindIII site in the pUC19 linker, dephosphorylated and the 1.8 kb pyrG containing fragment from pJers4 was inserted. The construction of pToC315 is illustrated in FIG. 3.

Figure 4:
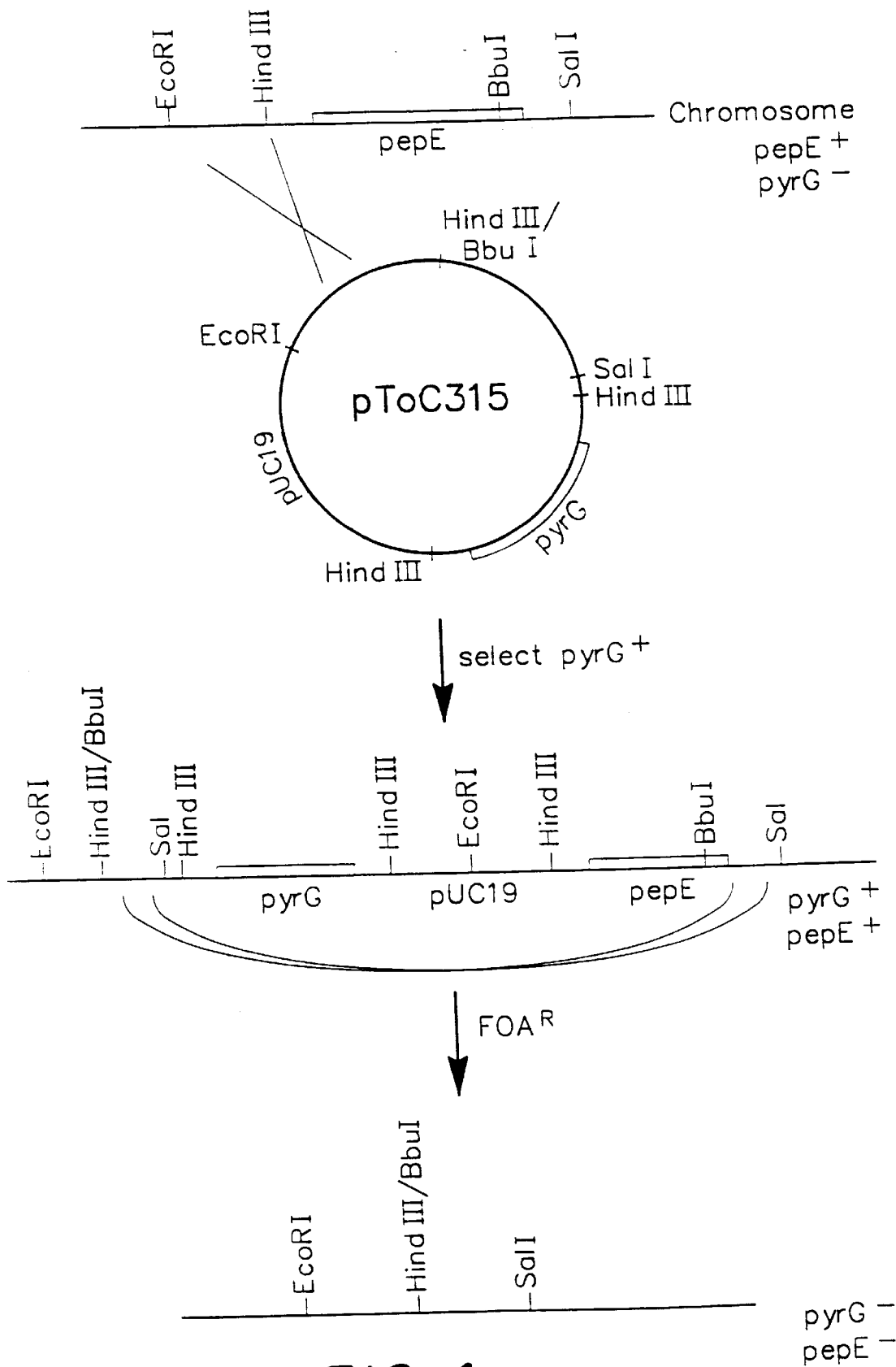
FIG. 4 diagrammatically shows a two step gene deletion of the pyrG gene.

HowB101 was transformed with pToC315 using standard procedures and transformants were selected by their ability to grow without the addition of uridine. After reisolation chromosomal DNA was prepared from 12 transformants, the DNA was cut with Asp718 and analysed by Southern analyses with a BbuI fragment from pToC301 containing part of the pepE gene as a radioactive labelled probe. One transformant had the plasmid integrated in the endogenous pepE gene as revealed by the disappearance of the pepE specific Asp718 fragment, which had been replaced by two new bands as predicted if pToC315 had integrated as a single copy by homologous recombination at the pepE locus. The transformant was named ToC1089. 5×10$^7$ conidiae spores of ToC1089 were spread on plates containing 5-fluoro-orotic acid selecting for loss of the pyrG gene. This is the second step in a two step gene deletion, the pyrG gene can be lost by recombination with either of two pairs of identical sequences, one of which will result in the deletion of the pepE gene as well. The procedure is depicted in FIG. 4. The frequency of 5-fluoro-orotic acid resistance was approximately 10$^{-5}$. The 5-fluoro-orotic acid resistant colonies were reisolated and a strain deleted for the pepE gene was identified by Southern analysis.

Example 2

Cloning and Disruption of the *Aspergillus oryzae* Serine Protease pepC

The *A. oryzae* pepC gene was cloned by cross-hybridization with the *A. niger* gene. The *A. niger* gene was obtained as a 1.1 kb PCR fragment from a PCR reaction with *A. niger* chromosomal DNA and pepC specific primers made according to the pepC sequence published by Frederick G. D et al. Gene 125 (1993) 57–64. The fragment was shown to contain pepC sequences by DNA sequencing. It hybridizes to *A. oryzae* chromosomal DNA under stringent conditions and Southern analysis showed that *A. oryzae* contains a single pepC like gene.

The pepC gene was deleted by a two step gene replacement method (G. May in "Applied Molecular Genetics of Filamentous Fungi" (1992) pp. 1–25. Eds. J. R. Kinghorn and G. Turner; Blackie Academic and Professional). As marker was used the *A. oryzae* pyrG gene, the *A. oryzae* strain was a pyrG$^-$ strain made by deletion of the pyrG gene.

Cloning of the *A. niger* Serine Protease pepC

From the published cDNA nucleotide sequence encoding *A. niger* pepC (Frederick G. D et al. Gene 125 (1993) 57–64)

two oligonucleotides were designed so that the encoding part of the pepC gene where amplified in a PCR reaction. The primer #5258 (5'-CTAGGATCCAAGGCATTT ATGAAGGGCATCCTCGGCCTTTCC) where made so that the 3' end of the nucleotide sequence corresponds to the N-terminal part of the pepC gene (underline) and the 5'-end is for facilitating cloning (contains a BamHI restriction endonuclease site). The primer #5259 (5'-CTACTCGAG TCAAAAAAAAACCAAGTCTTCCGATCTACG) where made so that the 3' end of the nucleotide sequence corresponds to the C-terminal part of the pepC gene and the 5'-end is for facilitating cloning (contains a XhoI restriction endonuclease site).

Genomic DNA from A. niger was used as template in the PCR reaction. Amplification reaction were performed in 100 μl volumes containing 2.5 units Taq-polymerase, 100 ng of A. niger genomic DNA, 50 mM KCl, 10 mM Tris-HCl pH 8.0, 1.5 mM MgCl$_2$, 250 nM of each dNTP, and 100 pM of each of the two primers described above.

Amplification was carried out in a Perkin-Elmer Cetus DNA Termal 480, and consisted of one cycle of 3 minutes at 94° C., followed by 25 cycles of 1 minutes at 94° C., 30 seconds at 55° C., and 1 minutes at 72° C. The PCR reaction produces one DNA fragment of ca. 1.1 kb in length. This fragment were isolated by gel electrophoresis, purified, cloned into the vector pCR$^6$II (Invitrogen Corporation), and sequenced using standard methods known in the art of molecular biology. The resulting plasmid were called pJaL197.

Cloning of the A. oryzae Serine Protease pepC

Southern blot of genomic DNA from A. oryzae IFO4177 where hybridized with the 1.1 kb $^{32}$P labelled EcoRI DNA fragment from pJaL197 clone containing the A. niger pepC gene. Genomic DNA was cut with the following restriction enzymes: EcoRI, BamHI, XhoI, and HindIII. Hybridization was carried out for 16 hours at 65° C. in 10×Denhart, 5×SSC, 0.02 M EDTA, 1% SDS, 0.15 mg/ml polyA and 0.05 mg/ml yeast tRNA. After hybridization the filters were washed in 2×SSC, 0.1% SDS at 65° C. twice and placed on X-ray films. The probe hybridized to a single size of fragment in each of the four digest, indicating that the pepC gene is present in a single copy in A. oryzae IFO4177.

Figure 5:
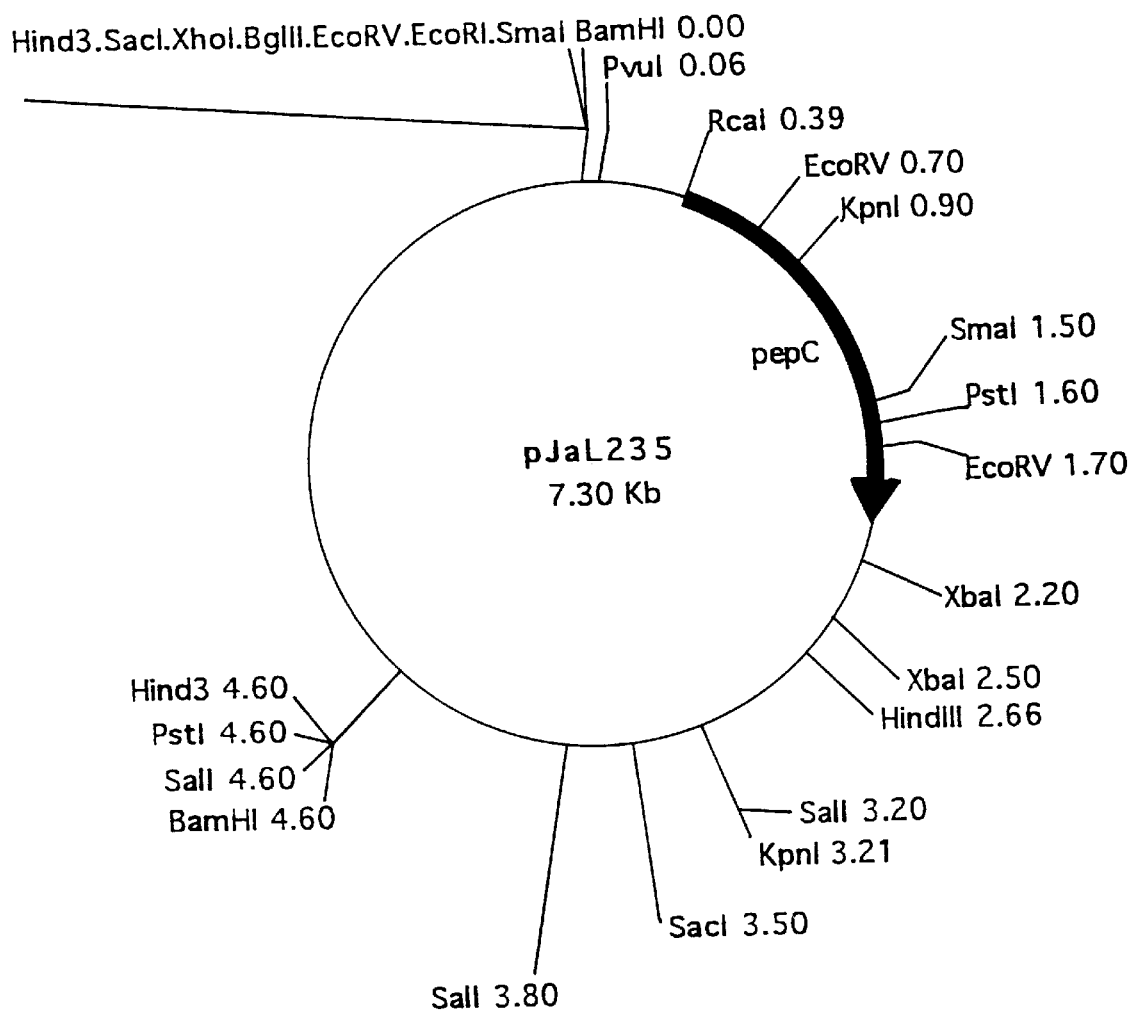
FIG. 5 shows the construction of pJaL235.

A partially library of A. oryzae genomic DNA was constructed containing BamHI fragments with a size of 4.5–5.5 kb and ligated into the vector pIC19H. The above A. niger pepC gene clone was radiolabelled and used to probe the partial A. oryzae BamHI genomic library. Hybridization was carried out as described above. About 4000 E. coli colonies were screened and four positive colonies was obtained. The 4 clones was shown to be identical by restriction enzyme digestion. One of these clones called pJaL235 (FIG. 5), with an insert of 4.6 kb, was analyses further by restriction mapping and Southern blotting. This shows that the pepC gene is located in a 2.9 kb BamHI/SalI fragment. Sequencing of this 2.9 kb BamHI/SalI fragment revealed the presence of a long open reading frame of 495 amino acids interrupted by two introns with consensus sequences indicative of intron splicing. The sequence of the A. oryzae pepC gene is shown in SEQ ID No. 3.

Construction of A. oryzae pyrG Gene Flanked by a Repeated Sequence

Figure 6:
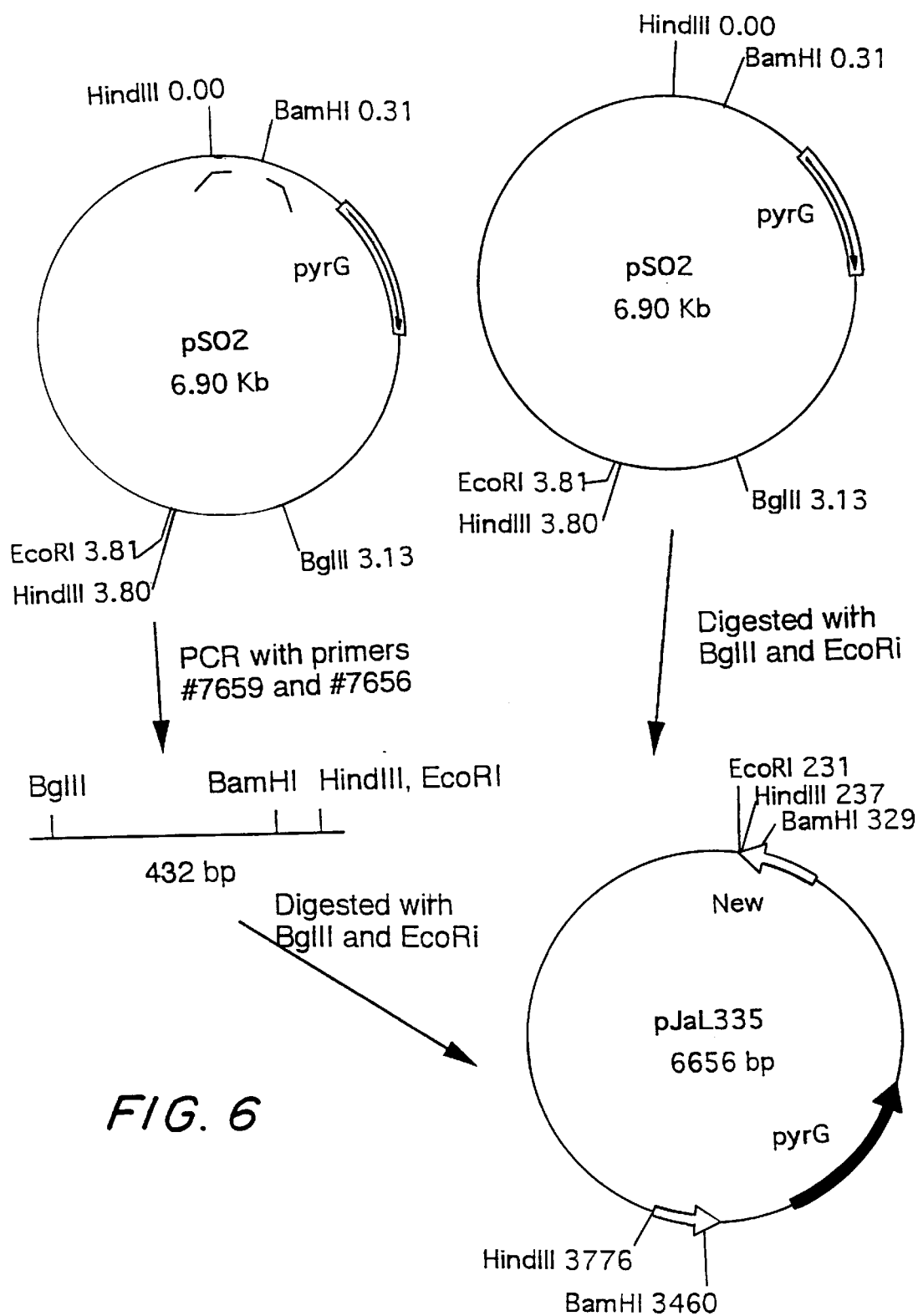
FIG. 6 shows the steps involved in the construction of pJaL335.

By PCR, With the Primer #7659 (5'-GGAGGAAGATCTCTCTCGTACTCTTCGATCTC), where the 3' end of the nucleotide sequence corresponds to position 7–26 in pSO2 (underline) and the 5'-end is for facilitating cloning (contains a BglII restriction endonuclease site), and the primer #7656 (5'-GGAGGAGAATTCAAGCTT CTTCTACATCACAGTTTGAAAGC), where the 3' end of the nucleotide sequence corresponds to position 385–407 in pSO2 (underline) and the 5'-end is for facilitating cloning (contains a EcoRI and HindIII restriction endonuclease site), on the plasmid pSO2 a 432 bp fragment was amplified. The fragment was digested with BglII and EcoRI and isolated by gel electrophoresis, purified, and cloned into the corresponding site in pSO2, resulting in plasmid pJaL335 (The construction is outlined in FIG. 6.

Construction of A. oryzae pepC Disruption Plasmid

Plasmid pJaL235 was digested with PvuI and treated with Klenow polymerase to make the ends blunt and then digested with HindIII. The 2.6 kb fragment were isolated by gel electrophoresis, and purified. The 2.6 kb fragment was cloned into pUC12 digested with SmaI and HindIII giving plasmid pJaL308.

Plasmid pJaL308 was digested with SmaI and treated with bacterial alkaline phosphatase to remove the 5' phosphate groups according to the manufacturers instructions and phenol extracted and precipitated.

Plasmid pSO2 was digested with HindIII, and treated with Klenow polymerase to make the ends blunt. The 3.8 kb fragment encoding the A. oryzae pyrG gene were isolated by gel electrophoresis, and purified.

Figure 7:
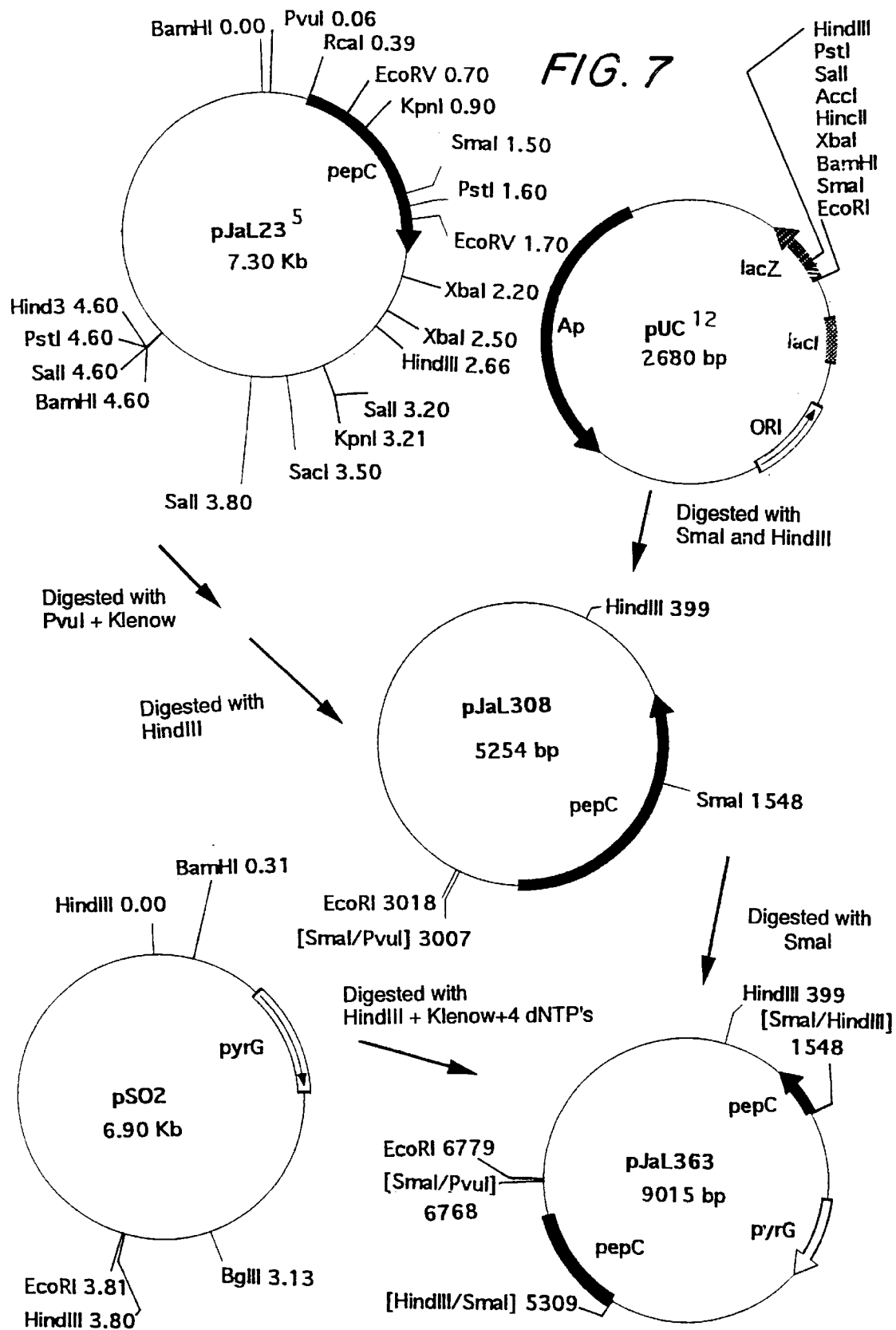
FIG. 7 shows the steps involved in the construction of pJaL363.

The two fragments are mixed together and ligated. After transformations of E. coli, the colonies carrying the correct plasmids are identified by restriction enzyme digestion of mini-plasmid preparations. The construction of pJaL363 is illustrated in FIG. 7.

Plasmid pJaL363 consist of pUC12 vector containing a fragment which carries the pepC gene flanked by an EcoRI site and an HindIII and where the pepC is interrupted by an 3.8 kb DNA fragment encoding the A. oryzae pyrG gene.

Figure 8:
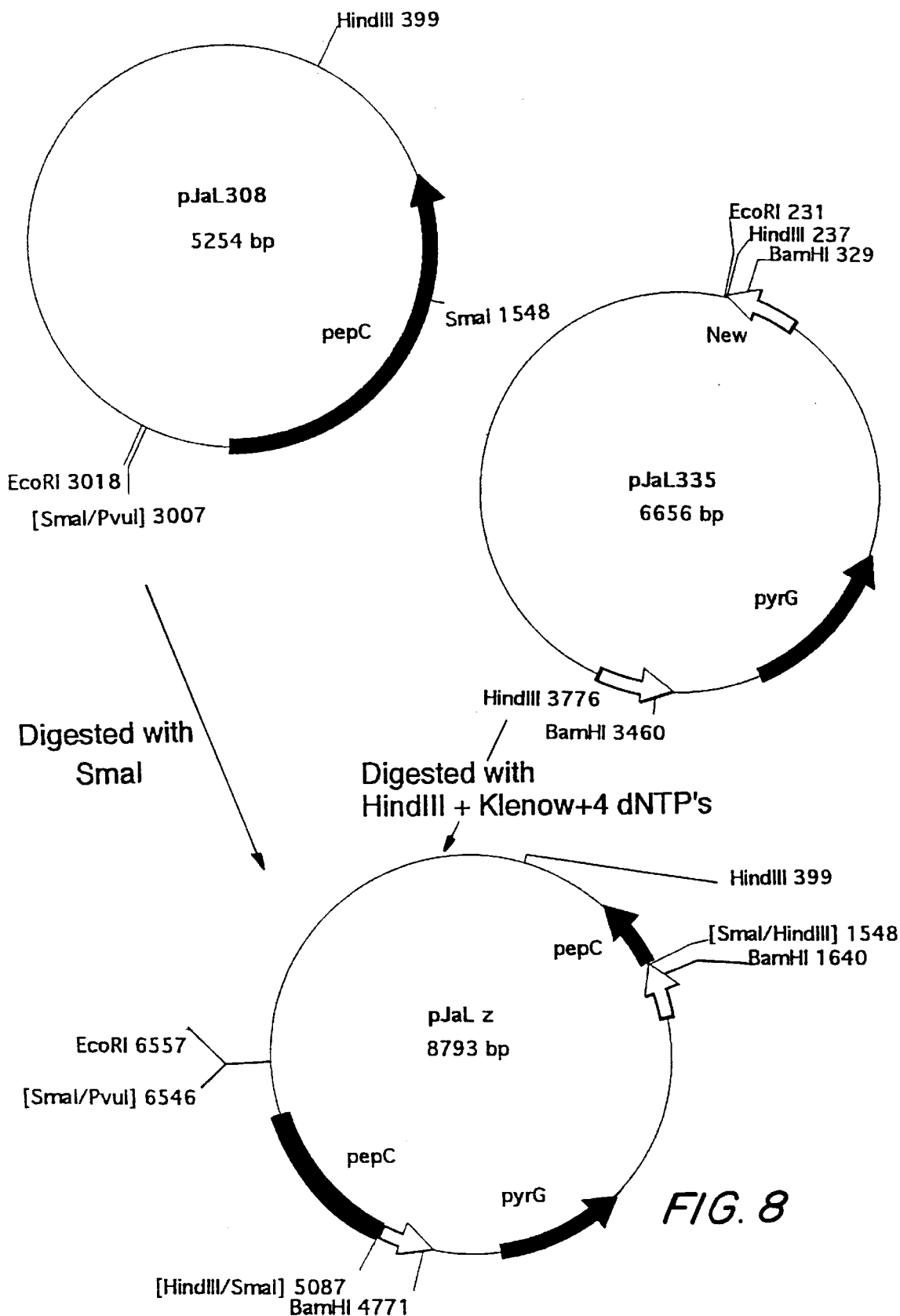
FIG. 8 shows the steps involved in the construction of pJaLz.

Plasmid pJaL335 is digested with HindIII, and treated with Klenow polymerase to make the ends blunt. The 3.5 kb fragment encoding the A. oryzae pyrG gene is isolated by gel electrophoresis, and purified. The fragment is cloned into pJaL308 SmaI restriction site. The construction of pJaLz is outlined in FIG. 8. The plasmid consist of pUC12 vector containing a fragment which carries the pepC gene flanked by an EcoRI site and an HindIII and where the pepC is interrupted by an 3.5 kb DNA fragment encoding the A. oryzae pyrG gene.

Transformation of A. oryzae Strain HowB101

15 μg of either one of the disruption plasmids is digested to completion by HindIII and EcoRI. The completeness of the digest is checked by running an aliquot on a gel and the remainder of the DNA is phenol extracted, precipitated and resuspended in 10 μl of sterile water.

The transformation of A. oryzae HowB101 host strain is preformed by the protoplast method (Christensen et al. Biotechnology (1988) 6: 1419–1422). Typically, A. oryzae mycelia is grown in a rich nutrient broth. The mycelia is separated from the broth by filtration. The enzyme preparation Novozyme® (Novo Nordisk) is added to the mycelia in osmotically stabilizing buffer such as 1.2 M MgSO$_4$ buffered to pH 5.0 with sodium phosphate. The suspension was incubated for 60 minutes at 37° C. with agitation. The protoplast is filtered through mira-cloth to remove mycelial debris. The protoplast is harvested and washed twice with STC (1.2 M sorbitol, 10 mM CaCl$_2$, 10 mM Tris-HCl pH 7.5). The protoplast is finally resuspended in 200–1000 μl STC.

For transformation 5 μg DNA is added to 100 μl protoplast suspension and then 200 μl PEG solution (60% PEG 4000, 10 mM CaCl$_2$, 10 mM Tris-HCl pH 7.5) is added and the mixture is incubated for 20 minutes at room temperature. The protoplast is harvested and washed twice with 1.2 M sorbitol. The protoplast is finally resuspended 200 ml 1.2 M sorbitol, plated on selective plates (minimal medium+10 g/l Bacto-Agar (Difco), and incubated at 37° C. After 3–4 days of growth at 37° C., stable transformants appear as vigorously growing and sporulating colonies.

Identification of a pepC Deletion Strain

From the stable colonies individual spores is streaked on fresh minimal plates. Single colonies is selected and restreaked to give pure cultures. These are used to inoculate 10 ml of liquid YPM medium (1% yeast extract, 1% peptone, 2% maltose) . After 18 hours at 30° C. shaking at 180 rpm, the mycelia are harvested on filter paper. Mycelia is then transfer to an 2 ml eppendorf tube and freeze dried. After freeze drying DNA is prepared from the individual mycelia by grinding the mycelia to a fine powder with a pestle in the tube. This powder are resuspended in 0.5 ml of 50 mM EDTA pH 8.0, 0.2% SDS, 1 μl DEP by vortexing. These are incubate at 65° C. for 20 minutes. After this is added 0.1 ml 5 M KAc pH 6.5, the soluzion is mixed and incubated on ice for 5 minutes. The cell debris is separated from the DNA solution by centrifugation at 20.000 rpm for 5 minutes. 0.4 ml supernatant are precipitated with 0.3 ml isopropanol and centrifugated at 20.000 rpm for 10 minutes. The DNA pellet is redissolved in 100 μl of sterile TE buffer containing 0.1 mg/ml RNAaseA.

3 μg of each DNA is digested with EcoRI, fractionated by agarose gel electrophoresis, transferred to Immobilan-N membrane filters, and probe with the 1.5 kb $^{32}$P labelled NcoI DNA fragment from pJaL335 containing part of the pepC protease gene. Strains which carry a disruption of the pepC are easily recognized by that the wild type band on 3.6 kb is shifted to a 7.4 kb band in the transformant.

The disrupted A. oryzae pepC strain is made pyrG minus by selecting spontaneous mutant resistance to 5-fluoroorotic acid, a phenotype characteristic of pyrG mutants. Being a pyrG mutant the strain requires uridine for growth. The strain can be transformed with the wt pyrG gene by selection for the ability to grow without uridine.

Example 3

Construction of an *Aspergillus oryzae* areAΔ Strain

The areAΔ strain was constructed as follows. The areA gene from A. oryzae was cloned. A pyrG⁻ strain also deficient for either pepC or pepE or pepC plus pepE was transformed with a plasmid carrying the pyrg gene inserted between DNA fragments upstream and downstream from the areA gene. The coding region for areA was not present on the plasmid. Transformants were selected for their ability to grow in the absence of uridine and in the presence of chlorate. This double selection selects both for a functional pyrG gene and for areA minus. Strains obtained by this selection procedure were finally screened by Southern analysis to identify those in which the chromosomal areA gene was substituted by the pyrG gene.

Cloning of the areA Gene

Figure 9:
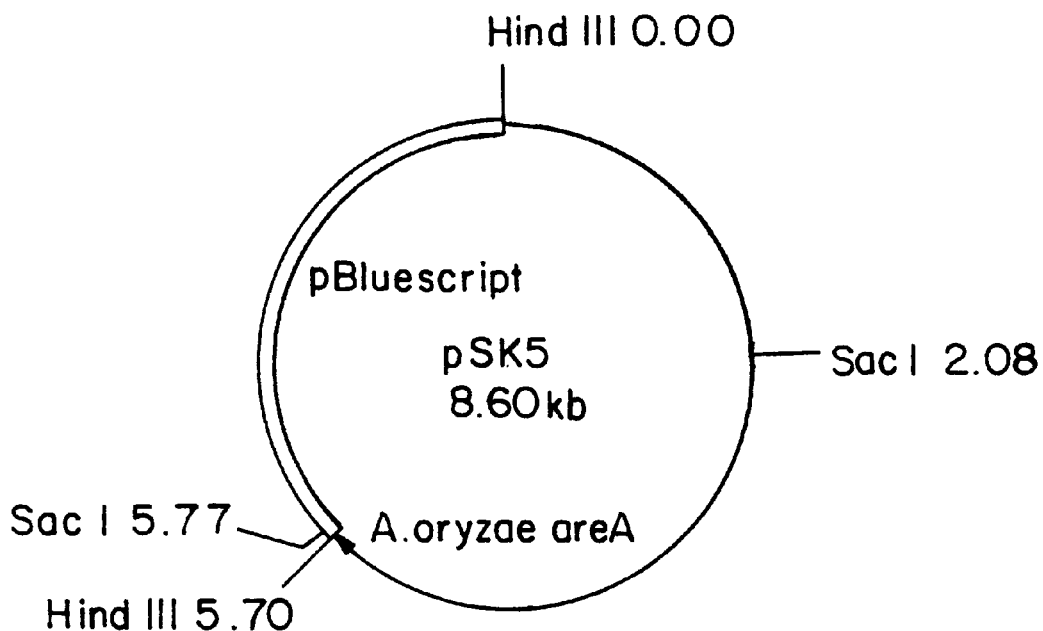
FIG. 9 shows the construction of pSK5 and pSK9.
Figure 9:
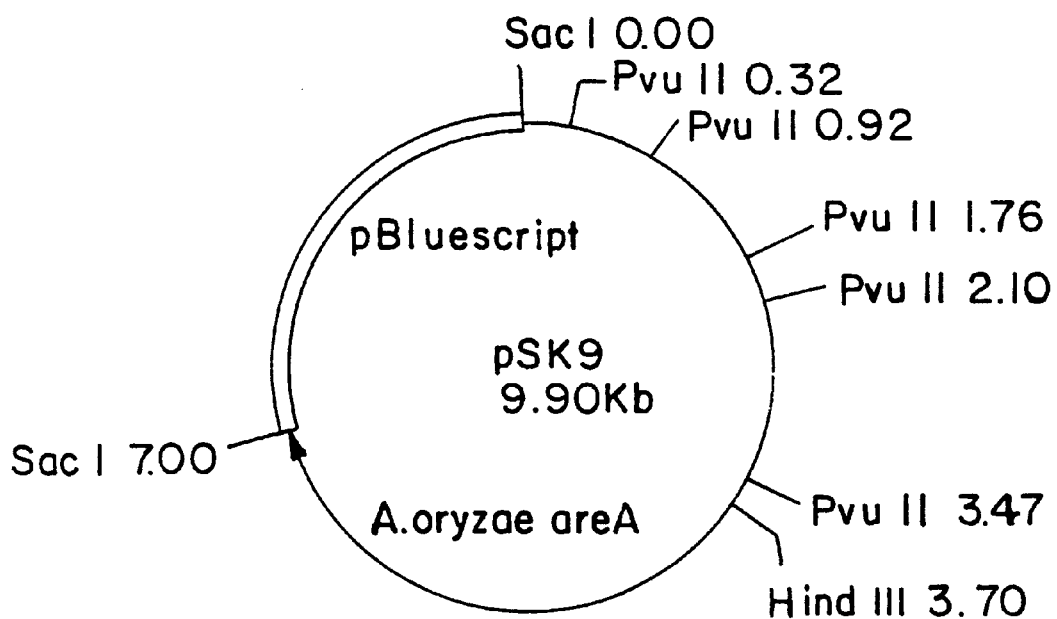

The A. oryzae areA gene was cloned by cross hybridization to the A. nidulans areA gene (B. Kudla et al., EMBO J. 9: 1355–1364 (1990)). A genomic library of A. oryzae IFO04177 was prepared by partial digestion of chromosomal DNA with SauIIIA and cloning of the obtained DNA fragments into the vector 1GEM-II (obtained from Promega). Cross hybridization of the library with the A. nidulans areA gene was performed in 40% formamide at 37° C. Hybridizing 1 clones were isolated and from these fragments were sub-cloned into the vector pBluescrip SK+ (obtained from Stratagene) giving rise to the plasmids pSK5 and pSK9 illustrated in FIG. 9. The cloned gene was able to complement an A. nidulans areA mutant, proving that it is indeed the A. oryzae areA homolog. 5643 bp of the clone was sequenced, and comparison of the sequences of the A. oryzae and the A. nidulans areA genes shows that they are highly homologous. The sequence of the A. oryzae areA gene is shown in SEQ ID No. 5.

Construction of the areA Deletion Plasmid

Figure 10A:
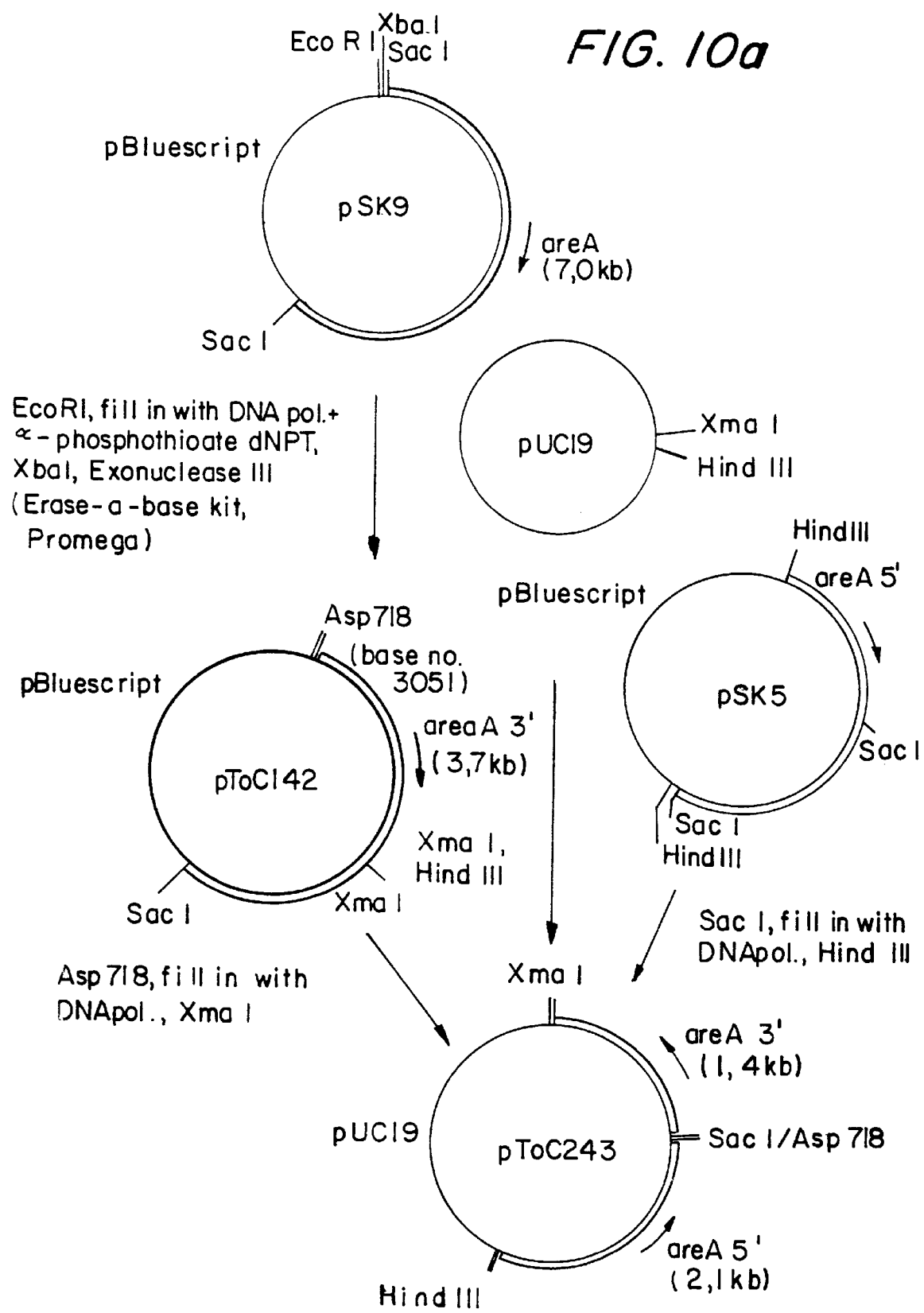
FIGS. 10a and 10b show the steps involved in the construction of pToC243 and pToC266.
Figure 10B:
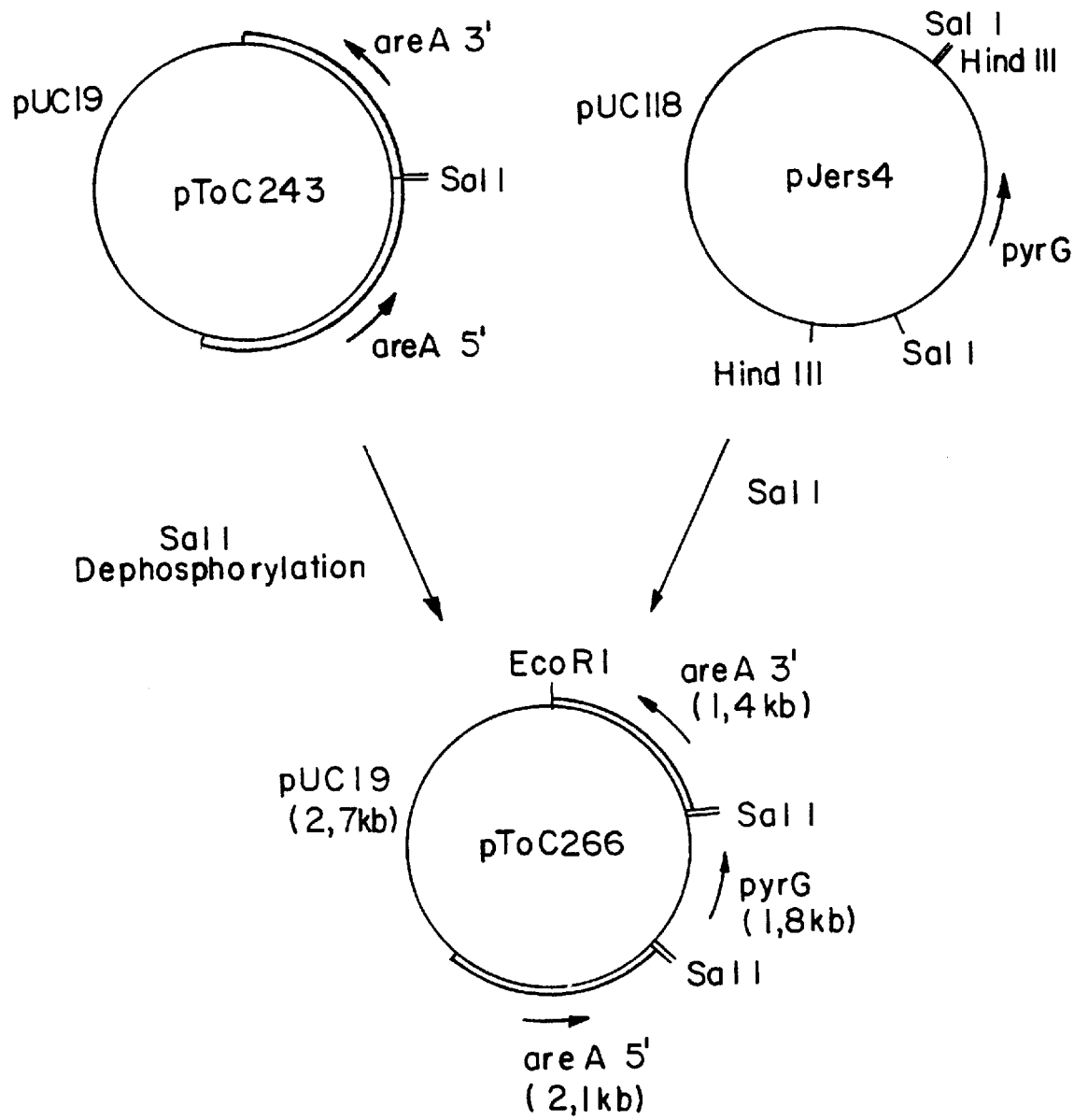

In order to delete the areA gene from the A. oryzae chromosome the plasmid pToC266 was constructed. pToC266 contains a 2.1 kb DNA fragment originating upstream of the areA gene (isolated from pSK5) and a 1.4 kb DNA fragment originating downstream from the areA gene (isolated from pSK9). The two fragments are separated by approximately 3.2 kb in the genome, the coding region is situated in this part of the gene. The A. oryzae pyrG gene from pJers4 was inserted between the areA upstream and downstream DNA fragments. The construction of pToC266 is illustrated in FIGS. 10a and 10b. pToC266 has a unique EcoRI site and was linearized by cutting with this restriction enzyme before used in transformations.

Selection of A. oryzae areA Strains

A pyrG⁻ strain also deficient for either pepC or pepE or pepC plus pepE is transformed with linearized pToC266. Transformants are selected on minimal plates (Cove Biochem. biophy. Acta (1966) 113: 51–56) containing glutamine as the nitrogen source and glucose as the carbon source. Transformants are reisolated twice on the same type of plates, and then subjected to growth test on different nitrogen sources. Transformants growing well on glutamine but not on nitrate, ammonium or urea are expected to be deleted for areA. The deletion is confirmed by Southern analysis.

Example 4

Construction of pMT1606

A plasmid containing the bar gene from *Streptomyces hygroscopius* (C. J. Thompson et. al, EMBO J. 6: 2519–2523 (1987)) inserted after the A. oryzae TAKA-amylase promoter and followed by a fragment containing the transcriptional terminator and polyadenylation signal from the A. niger gla gene was constructed.

Figure 11:
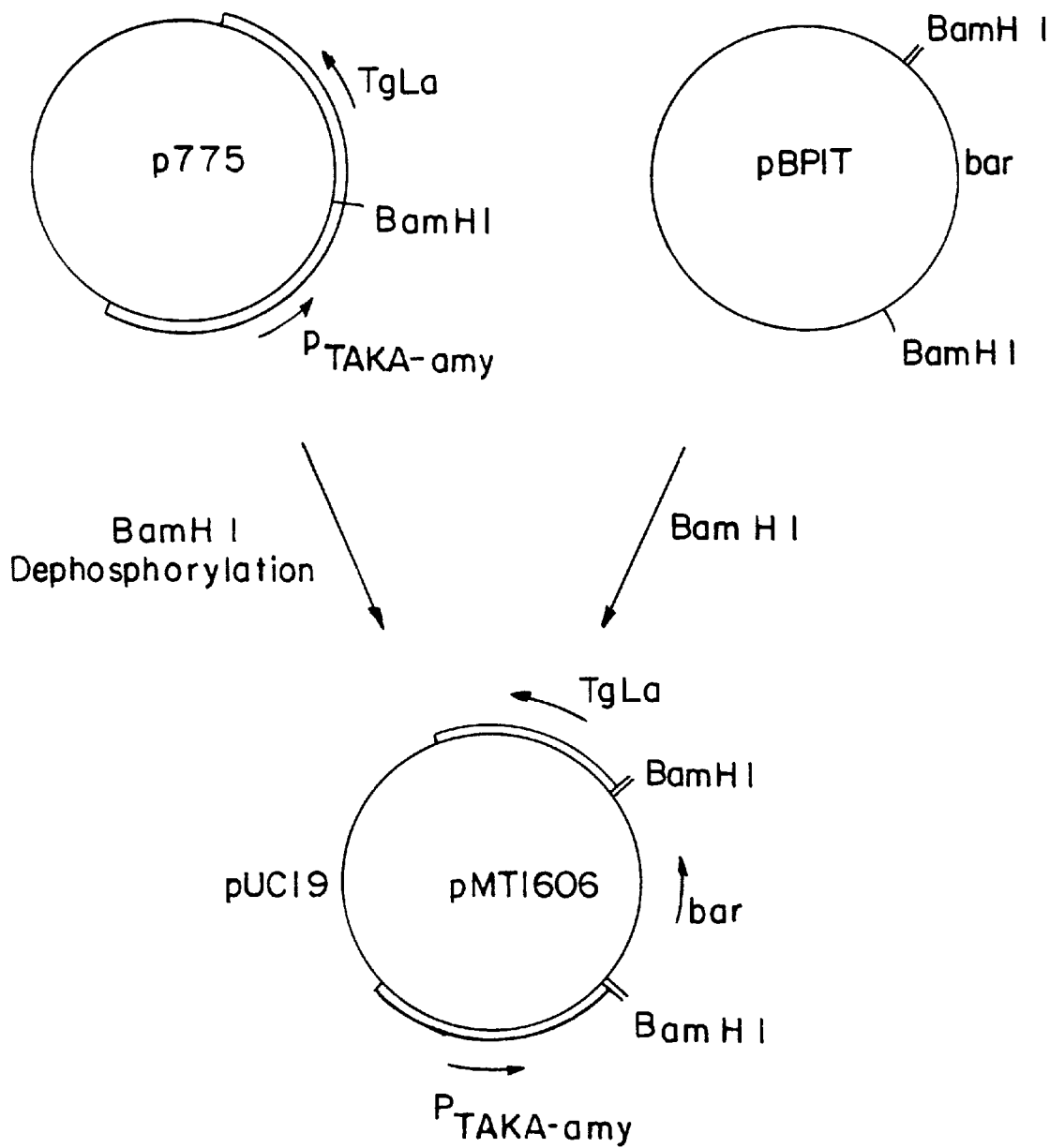
FIG. 11 shows the steps involved in the construction of pMT1606.

The plasmid, pMT1606, can be used for selection of glufosinate resistant transformants of A. oryzae . pMT1606 was constructed by isolating the bar gene from the plasmid pBP1T (B. Straubinger et. al, Fungal Genetics Newsletter 39: 82–83 (1992)) and cloning it into the fungal expression plasmid p775 described in EP publication No. 0 098 993 A1. FIG. 11 illustrates the construction of pMT1606.

Example 5

Production of Chymosin in A. oryzae (areAΔ, PepEΔ, pepC⁻)

Figure 12:
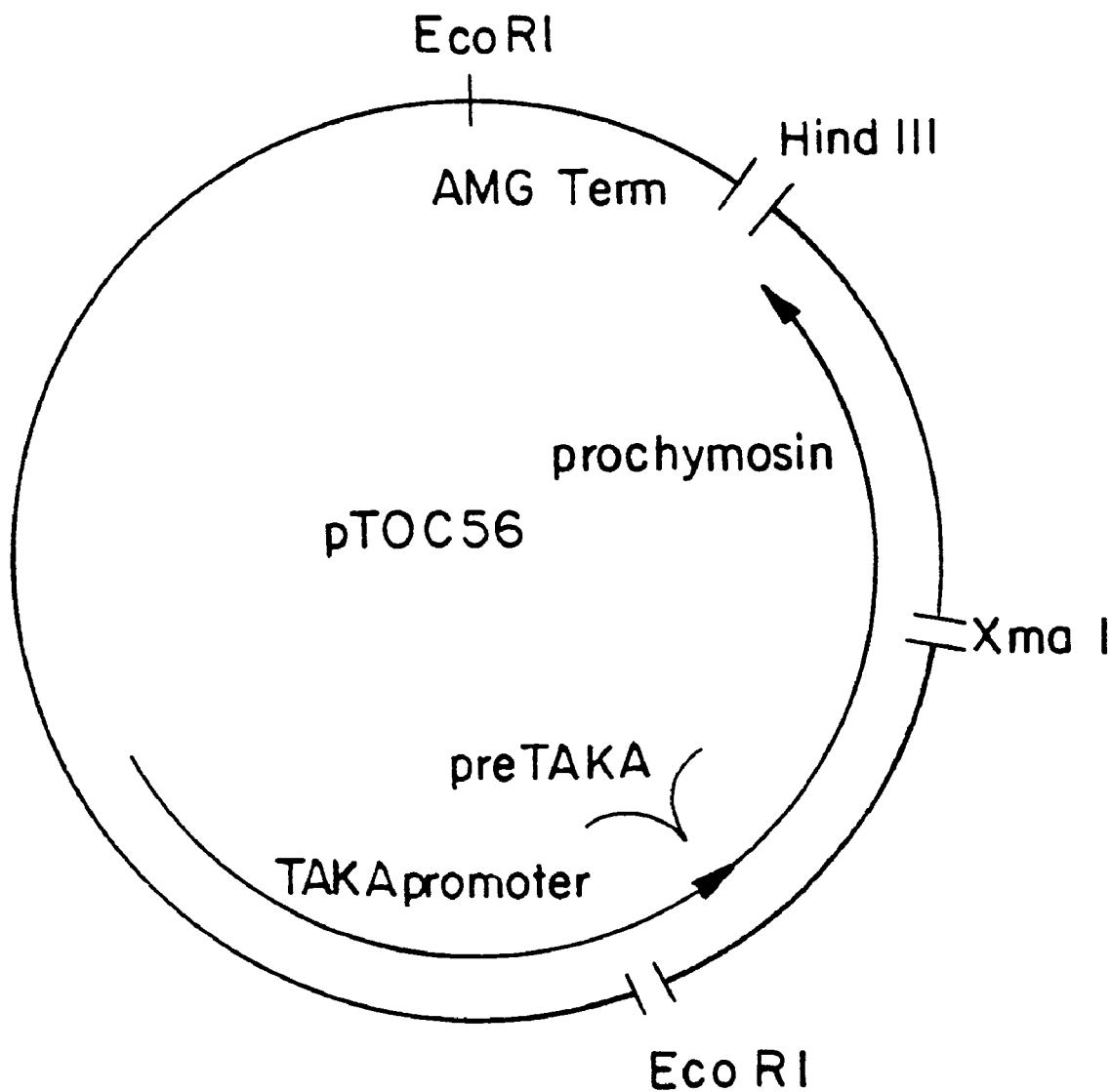
FIG. 12 shows the construction of pToC56.

An A. oryzae areAΔ, pepEΔ, pepC⁻ strain is transformed with the plasmid pToC56 (FIG. 12), which is a fungal expression plasmid for the mammalian enzyme chymosin, by co-transformation with pMT1606. Construction of the plasmid pToC56 is described in EP publication No. 0 98 993.

Transformants are selected for growth on minimal medium containing 10 mM ammonium and 1 mg/ml glufosinate and screened for the presence of pToC56 by the ability to produce chymosin. The transformants are grown in shake flasks in minimal medium containing maltodextrin and glutamine for 4 days at 30° C. The content of chymosin in the supernatants were analysed by SDS-Page and Western blotting.

Example 6
Production of PepC in *A. oryzae*

Construction of an expression plasmid for pepC. Plasmid pJaL235 was digested with AatII and NsiI and treated with Klenow polymerase to make the ends blunt. The 1.7 kb fragment was isolated by gel electrophoresis, and purified. The 1.7 kb fragment was cloned into pIC19H digested with SmaI giving pJaL365.

Figure 13A:
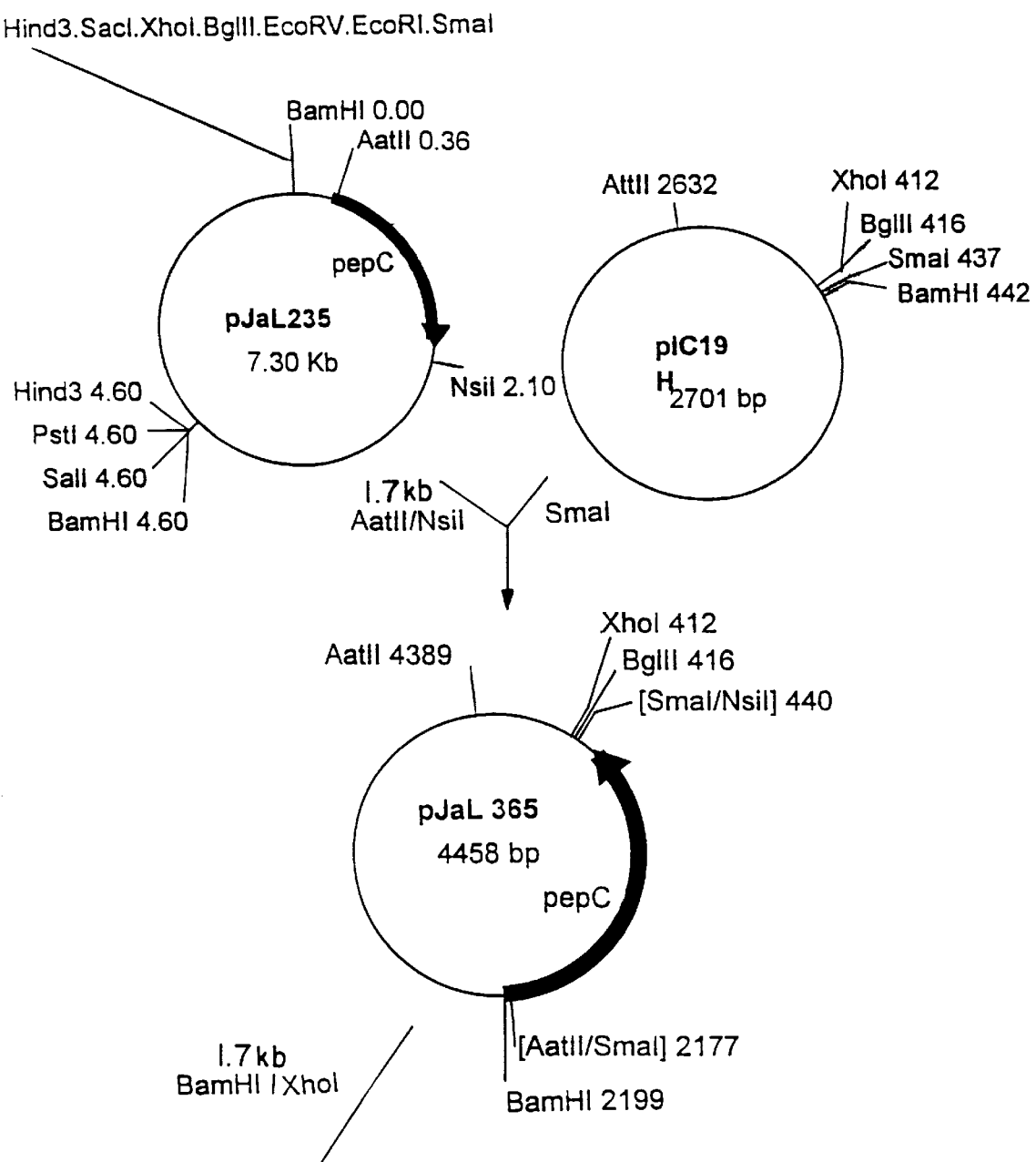
FIGS. 13a and 13b show the steps involved in the construction of pJaL368.
Figure 13B:
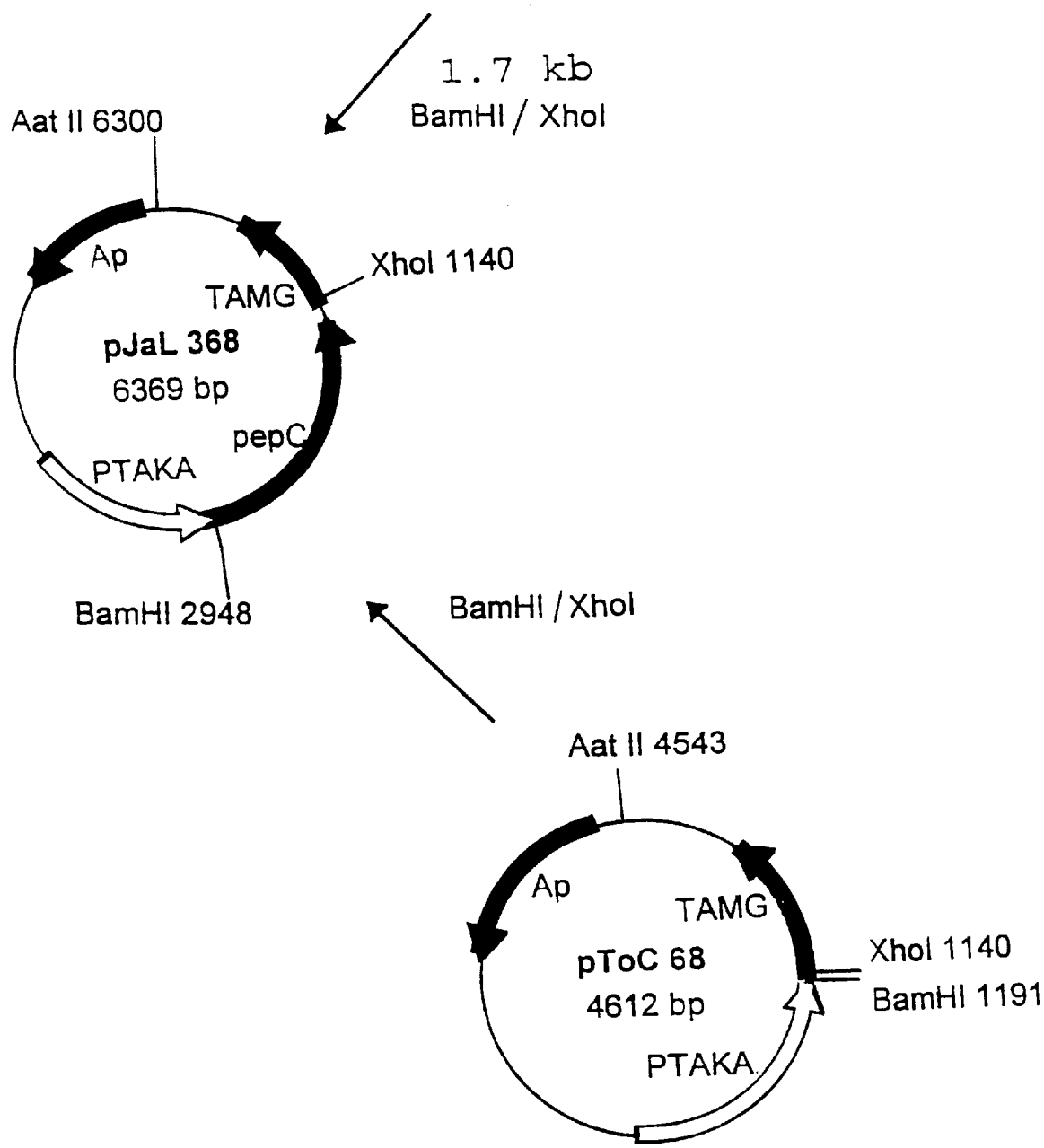

Plasmid pJaL365 was digested with BamHI and XhoI and the 1.7 kb fragment was isolated by gel electrophoresis, and purified. The 1.7 kb fragment was cloned into pToC68 digested with BamHI and XhoI giving pJaL368 (FIGS. 13a and 13b).

An *A. oryzae* strain is transformed with the plasmid pJaL368, which is a fungal expression plasmid for the protease PepC, by cotransformation with pToC90.

Transformants are selected for growth on minimal medium containing 10 mM acetamide and screened for the presence of pJaL368 by the ability to produce the protease PepC.

Example 7
Overexpression of PepE

Figure 14A:
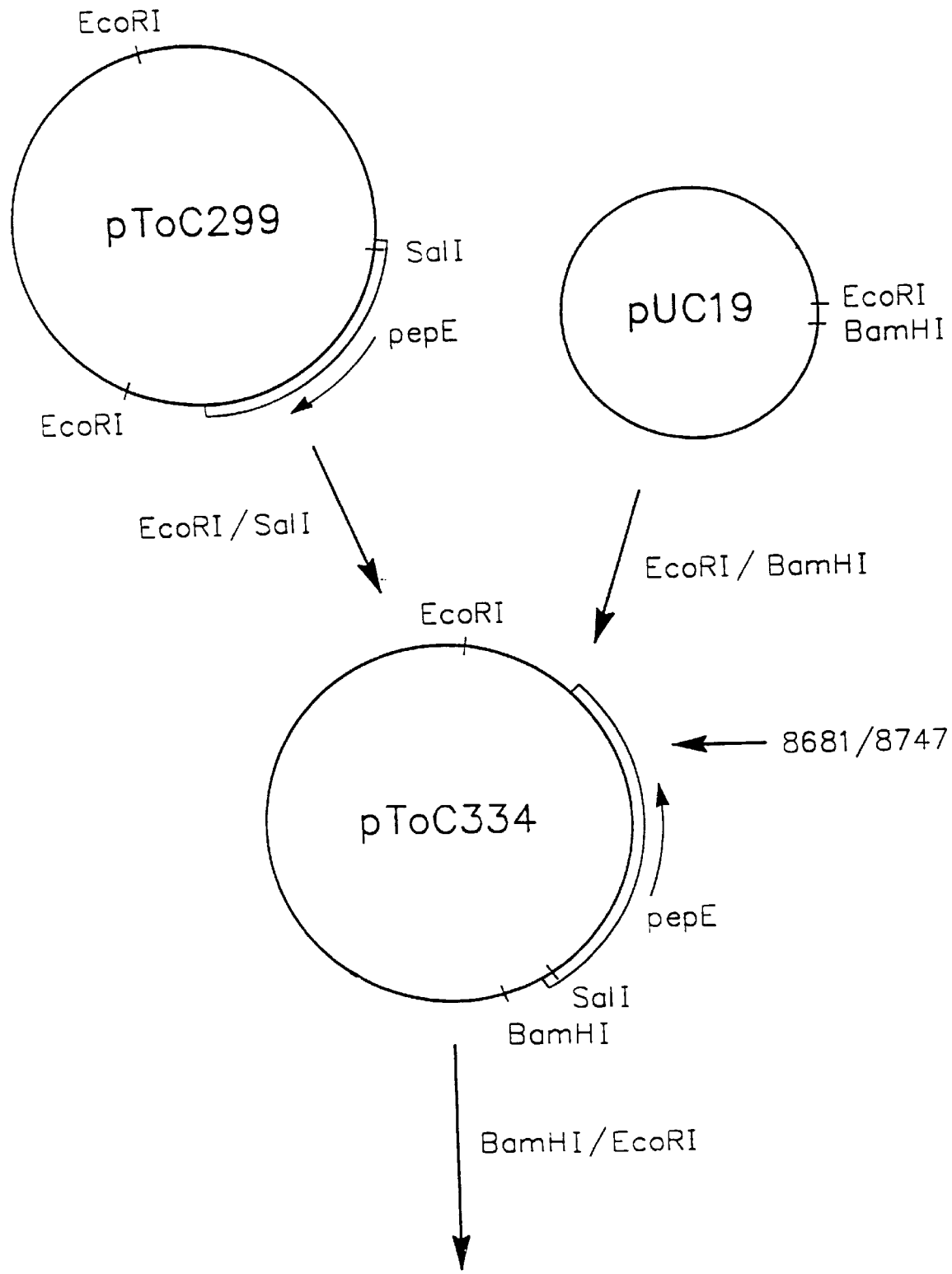
FIGS. 14a and 14b show the construction of pToC338.
Figure 14B:
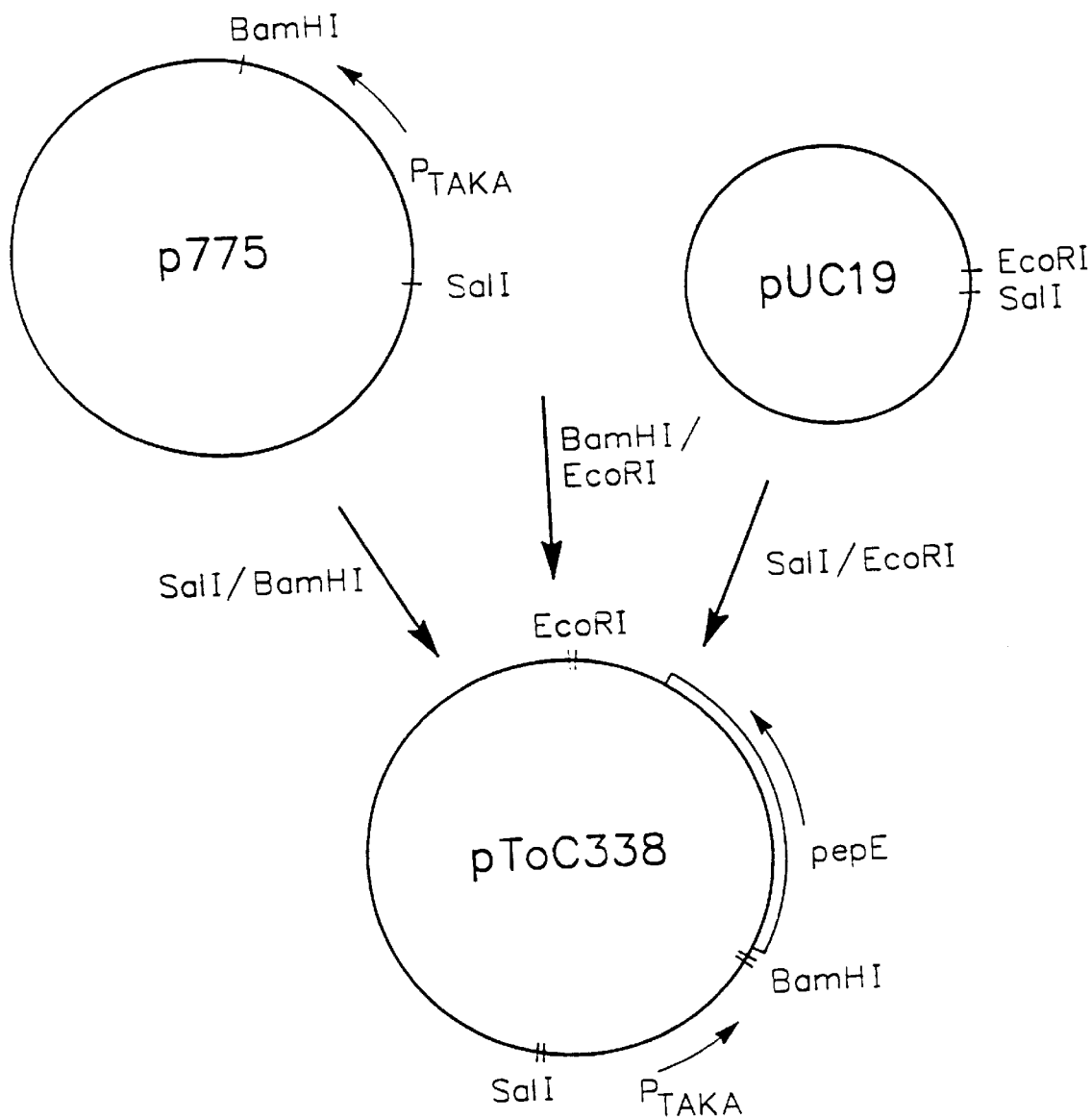

A plasmid called pToC338 carrying the pepE gene fused to the TAKA-amylase promoter from *A. oryzae* was constructed. FIGS. 14a and 14b depicts the construction.

An EcoRI/SalI fragment from pToC299 containing most of the coding region and appr. 430 bp of the 3' untranslated region of pepE was cloned into EcoRI/BamHI cut pUC19 together with a synthetic DNA fragment. of the following sequence:

```
8681 GATCCACCATGAAG

8747 GTGGTACTTCAGCT
```

The resulting plasmid called pToC334 was cut with BamHI/EcoRI and a fragment containing the entire structural gene of pepE with a BamHI site fused immediately upstream of the start codon was isolated, approximately 430 bp of untranslated 3' sequence was also present in the fragment. The fragment was cloned into EcoRI/SalI cut pUC19 together with an approximately 1.1 kb SalI/BamHI fragment from the plasmid p775 containing the TAKA-amylase promoter from *A. oryzae*. The resulting plasmid was named pToC338.

pToC338 was co-transformed into *A. oryzae* JaL125 (an *A. oryzae* alp minus strain described in Danish Patent Application No. 0354/96) with pToC90, which contains the *A. nidulans* acetamidase (amdS) gene, using standard procedures (e.g. as described in EP 0 098 993 A1). Transformants were selected by their ability to use acetamide as the sole nitrogen source. 11 transformants were reisolated twice through conidiospores. The transformants were fermented for three days at 30° C. in 10 ml YPM (YP with 2% maltose) and the fermentation broth was analysed by SDS-page. One of the transformants produced a protein of the same size as the protein encoded by the pepE gene, protease activity measurements confirmed that the broth from that transformant contained a higher activity toward casein at pH=5.5 compared to the host strain JaL125. The protein was purified and N-terminal sequencing showed that it is indeed the protein encoded by the pepE gene. The N-terminal of the secreted protein was:

gly\*-arg-his-asp-val-leu-val-asp-asn-phe-leu-asn-ala-gln-tyr-phe-ser-glu-ile-glu-ile-gly-thr-pro-pro-gln-lys-phe-lys \* this residue could also be a lysine.

confirming the expression of the PepE protease.

---

What is claimed is:

1. A modified fungus wherein: (i) the areA gene no longer expresses a functional AreA activator, and (ii) genes encoding PepC and/or PepE no longer express functional PepC and/or PepE proteases.

2. The fungus of claim 1, wherein said modification comprises deletion of all or parts of the areA, pepC, and/or pepE genes.

3. The fungus of claim 2, wherein said modification comprises deletion of all or parts of the areA and pepE genes.

4. The fungus of claim 1, wherein said modification comprises interfering with the regulation of the expression signals regulating the expression of the areA, pepC, and/or pepE genes themselves.

5. The fungus of claim 4, wherein said modification comprises interfering with the regulation of the expression signals regulating the expression of the areA and pepE genes themselves.

6. The fungus of claim 1, wherein said modification is achieved by expressing antisense nucleic acids that inhibit expression of the areA pepC, and/or pepE genes.

7. The fungus of claim 1, wherein said modification comprises inserting extra DNA internally in the areA, pepC, and/or pepE genes.

8. The fungus of claim 1 which is a filamentous fungus belonging to a genus selected from the group consisting of Aspergillus, Trichoderma, Humicola, Candida, Acremonium, Fusarium, and Penicillium.

9. The fungus of claim 8, which belongs to a species selected from the group consisting of *A. oryzae, A. niger, A. awamori, A. phoenicis, A. japonicus, A. foetidus, A. nidulans, T. reesei, T. harzianum, H. insolens, H. lanuginosa, F. graminearum, F. solani,* and *P. chrysogenum.*

10. A method for producing a fungus according to claim 1, said method comprising:

i) cloning the areA, pepC, and/or pepE genes from a fungus of interest;

ii) producing DNA constructs each comprising one among the areA gene, the pepC gene, and/or the pepE gene, wherein an internal part has been substituted, deleted, or extra DNA has been inserted;

iii) transforming said fungus with the constructs; and iv) isolating transformants which are areA− pepC−, areA− pepE−, or areA−pepC−pepE−.

11. A method for producing a fungus according to claim 1, said method comprising:

i) cloning the areA and pepE genes from a fungus of interest;

ii) producing DNA constructs each comprising one among the areA gene and the pepE gene, wherein an internal part has been substituted, deleted, or extra DNA has been inserted;

iii) transforming said fungus with the constructs; and iv) isolating transformants which are areA− pepE−.

12. A method for producing a fungus according to claim 1, said method comprising:
   i) cloning of the areA and pepC genes from a fungus of interest;
   ii) producing DNA constructs each comprising one among the areA gene and the pepC gene, wherein an internal part has been substituted, deleted, or extra DNA has been inserted;
   iii) transforming said fungus with the constructs; and
   iv) isolating transformants which are areA$^-$ pepC$^-$.

13. A process for the production of a desired gene product, said process comprising: (i) cultivating a fungus according to claim 1 in a suitable growth medium at appropriate conditions and (ii) recovering and purifying the desired gene product.

14. A method for producing a fungus according to claim 1, said method comprising:
   i) transformation of a host fungus with expression plasmids which give rise to synthesis of an RNA molecule complementary to the mRNA transcribed from the areA gene, the pepC gene, and/or the pepE gene and a suitable marker, either on separate plasmids or on the same plasmid;
   ii) selection of transformants using said marker; and
   iii) screening selected transformants for strains exhibiting a reduction in the synthesis of the AreA, PepC, and/or PepE products.

15. A method for producing a fungus according to claim 1, said method comprising:
   i) transformation of a host fungus with expression plasmids which give rise to synthesis of an RNA molecule complementary to the mRNA transcribed from the areA gene and the pepE gene and a suitable marker, either on separate plasmids or on the same plasmid;
   ii) selection of transformants using said marker; and
   iii) screening selected transformants for strains exhibiting a reduction in the synthesis of the AreA and PepE products.

16. The process of claim 13, wherein said desired gene product is an industrial peptide or protein.

17. A process for the production of a desired gene product, said method comprising: (i) cultivating a fungus according to claim 1, wherein said fungus has been transformed to integrate a DNA sequence coding for the desired gene product into the genome of the fungus in a functional manner, in a suitable growth medium at appropriate conditions and (ii) recovering and purifying the desired gene product.

18. A process for producing a desired polypeptide, said process comprising (i) cultivating a fungus in an appropriate growth medium and (ii) recovering said polypeptide from said culture, wherein said fungus comprises a recombinant DNA construct capable of causing expression of said polypeptide or a precursor thereof in said fungus, and wherein said fungus (a) produces lower amounts of functional AreA protein, and (b) produces lower amounts of PepC and/or PepE protein than the wild-type of said fungus.

19. A method according to claim 18, wherein said fungus has been modified to produce lower than wild-type amounts of AreA, PepC, and/or PepE by a process comprising transforming a parent of said fungus with DNA constructs capable of causing reduced production of functional AreA, PepC, and/or PepE when integrated in the genome of said fungus.

20. A method according to claim 18, wherein said polypeptide is secreted to the extracellular medium by said fungus.

21. A method according to claim 18, wherein said fungus produces higher amounts of said polypeptide than a similar fungus where said similar fungus produces AreA, PepC, and/or PepE in amounts similar to those produced by the wild-type of said fungus, said similar fungus being identical to said fungus in all other respects.

22. The process of claim 13, wherein said gene product is a secreted protein.

23. The process of claim 16, wherein said desired gene product is an enzyme.

24. The process of claim 23, wherein said enzyme is selected from the group consisting of protease, lipase, cutinase, cellulase, and chymosin.

25. The process of claim 13, wherein said desired gene product is a therapeutically active peptide or protein.

26. The process of claim 25, wherein said therapeutically active peptide or protein is selected from the group consisting of insulin, growth hormone, glucagon, somatostatin, interferon, PDGF, factor VII, factor VIII, urokinase, tPA, EPO, and TPO.

27. A gene product produced in accordance with claim 13.

28. A DNA sequence coding for the pepC gene from A. oryzae (SEQ ID No. 1).

29. A PepC protease from A. oryzae (SEQ ID No. 2).

30. A process for the production of the PepC protease of claim 29 comprising transforming a suitable host with a DNA construct comprising a DNA sequence of claim 28, selecting a transformant capable of producing said PepC protease, cultivating said transformant in an appropriate growth medium and recovering said PepC protease from said culture.

31. A DNA sequence coding for the pepE gene from A. oryzae (SEQ ID No. 3).

32. A PepE protease from A. oryzae (SEQ ID No. 4).

33. A process for the production of the PepE protease of claim 32 comprising transforming a suitable host with a DNA construct comprising a DNA sequence of claim 31, selecting a transformant capable of producing said PepE protease, cultivating said transformant in an appropriate growth medium and recovering said PepE protease from said culture.

34. The process of claim 30, wherein said host is a fungus, according to claim 1.

35. The process of claim 30, wherein said host is A. oryzae, and wherein said DNA construct comprising a DNA sequence of claim 28, provides for an extra copy of the gene encoding said PepC or PepE protease.

* * * * *